(12) United States Patent
Joy et al.

(10) Patent No.: US 10,106,514 B2
(45) Date of Patent: Oct. 23, 2018

(54) THERMORESPONSIVE POLYESTERS

(71) Applicants: Abraham Joy, Copley, OH (US); John Swanson, Akron, OH (US)

(72) Inventors: Abraham Joy, Copley, OH (US); John Swanson, Akron, OH (US)

(73) Assignee: The University of Akron, Akron, OH (US)

(*) Notice: Subject to any disclaimer, the term of this patent is extended or adjusted under 35 U.S.C. 154(b) by 0 days.

(21) Appl. No.: 14/811,238

(22) Filed: Jul. 28, 2015

(65) Prior Publication Data

US 2016/0024251 A1 Jan. 28, 2016

Related U.S. Application Data

(60) Provisional application No. 62/029,683, filed on Jul. 28, 2014.

(51) Int. Cl.
| | |
|---|---|
| C08G 63/685 | (2006.01) |
| C07D 295/16 | (2006.01) |
| C07C 235/08 | (2006.01) |
| C07C 235/14 | (2006.01) |
| C08G 73/02 | (2006.01) |

(52) U.S. Cl.
CPC .......... C07D 295/16 (2013.01); C07C 235/08 (2013.01); C07C 235/14 (2013.01); C08G 63/6856 (2013.01); C08G 73/0233 (2013.01); C07C 2101/02 (2013.01)

(58) Field of Classification Search
CPC .................................................. C08G 63/6856
See application file for complete search history.

(56) References Cited

U.S. PATENT DOCUMENTS

2012/0116424 A1 * 5/2012 Lee ........................ A61L 24/046
606/151

FOREIGN PATENT DOCUMENTS

WO WO 2013130985 A1 * 9/2013 ......... C08G 63/6856

* cited by examiner

*Primary Examiner* — Michael F Pepitone
(74) *Attorney, Agent, or Firm* — Renner Kenner Greive Bobak Taylor & Weber

(57) ABSTRACT

A thermoresponsive polyester comprising units derived from an amide functional diol compound having a first amide group having a nitrogen atom and a carbonyl group; a second amide group tethered directly or indirectly through an organic group at the carbonyl group of the first amide group; and two organic groups terminated with a hydroxyl group attached to the nitrogen atom of the first amide group. The thermoresponsive polyesters exhibit a lower critical solution temperature at which they undergo a thermally induced reversible hydrophobicity change. This hydrophobicity change may involve the formation of coacervates of the thermoresponsive polyesters which can then coalesce into a precipitated polymer rich phase.

17 Claims, 8 Drawing Sheets

TR-PyrPE

TR-DEPE

TR-iPrPE

TR-CPPE

TR-nPrPE

Polyoxaxolines

| PiPOx | PnPrOx |
|---|---|
| 36 | 24 |

Polyacrylamides

| PNCPAM | PVPy | PDEAM | PNIPAM | PNNPAM |
|---|---|---|---|---|
| 53 | 51 | 33 | 32 | 10 |

Polymer LCST or $T_{cp}$ (°C)

Fig. 2

THERMORESPONSIVE POLYESTERS

CROSS-REFERENCE TO RELATED APPLICATIONS

This application claims priority from U.S. provisional patent application Ser. No. 62/029,683 filed on Jul. 28, 2014, which is incorporated herein by reference in its entirety.

STATEMENT REGARDING FEDERALLY SPONSORED RESEARCH OR DEVELOPMENT

This invention was made with government support under Grant #2012141051 awarded by National Science Foundation. The government has certain rights in the invention.

FIELD OF THE INVENTION

One or more embodiments provides thermoresponsive polyesters prepared from amide pendant functionalized diols. The thermoresponsive polyesters have a lower critical solution temperature at which they undergo a thermally induced reversible hydrophobicity change.

BACKGROUND OF THE INVENTION

Stimuli-responsive, or "smart materials," have found wide acceptance across a variety of fields due to their ability to exhibit a significant change in physical properties as a result of a minor change in external stimuli such as light, electric potential, pH, redox, magnetic field, pressure, or temperature. Temperature sensitive polymers, mainly represented by poly(N-isopropylacrylamide) (PNIPAM)3-4 and polyoxazolines (POx)5-6, undergo a thermally induced reversible hydrophobicity change at a lower critical solution temperature (LCST). Above the LCST, certain thermoresponsive polymers such as PNIPAM undergo a coil-globule transition that results in significant dehydration of the polymer. The dehydrated polymers then aggregate due to hydrophobic interactions and the solution optically changes from clear to opaque. The temperature at which this observable macroscopic transformation occurs is defined as the cloud point temperature (Tcp) and is often used as a qualitative measure of the LCST. Not all temperature responsive polymers undergo the coil-globule transition exhibited by PNIPAM. Instead, some polymers display an incomplete dehydration when brought above the LCST. The partially dehydrated polymers then separate into polymer-rich coacervate droplets within a polymer-deficient liquid phase. Similar to coil-globule transition-type polymers, coacervate-type polymers exhibit a thermally reversible cloud point in solution. Coacervate-type polymers are particularly attractive from a biomaterials standpoint since their incomplete dehydration leads to minimal conformational change as compared to coil-globule polymers. This prevents coacervate-type polymers from damaging sensitive biomolecules and thus allows them to be used as agents for the purification of proteins and nucleic acid without disrupting their function, as controlled delivery agents for sensitive physiologically active molecules, and as injectable scaffolds. Despite this advantage, there have been far fewer reports in literature on thermoresponsive coacervate-type polymers as compared to coil-globule type polymers.

Polymeric degradation is a desirable quality for numerous medical applications but is not achievable with many common thermoresponsive polymers, such as polyacrylamides. Polyamides and synthetic poly(amino acids) exhibit biodegradation due to the gradual hydrolysis of the amide backbone. However, the slow degradation may be limiting for applications where a faster degrading material, such as those based on a more hydrolysable ester bond, would be desirable. Thermoresponsive polyphosphoesters and polyesters do exist in the literature, but suffer from limited side chain functionality and few are able to form coacervates.

Thus, there presently exists a need in the art to for a biodegradable, theroresponsive polymers.

SUMMARY OF THE INVENTION

One or more embodiments provides a thermoresponsive polyester comprising: a first amide group having a nitrogen atom and a carbonyl group; a second amide group tethered directly or indirectly through an organic group at the carbonygroup of the first amide group; and the nitrogen atom of the first amide group is part of the backbone of the polyester.

Another embodiment provides a composition comprising: an aqueous solution, and dispersed in the a thermoresponsive polyester comprising a first amide group having a nitrogen atom and a carbonylgroup; a second amide group tethered directly or indirectly through an organic group at the carbonyl group of the first amide group; and the nitrogen atom of the first amide group is part of the backbone of the polyester.

Another embodiment provides a thermoresponsive polyester comprising: units derived from a dicarboxylic acid; and units derived from an amide functional diol compound comprising a first amide group having a nitrogen atom and a carbonyl group; a second amide group tethered directly or indirectly through an organic group at the carbonyl group of the first amide group; and two organic groups terminated with a hydroxyl group attached to the nitrogen atom of the first amide group.

Another embodiment provides an amide functional diol compound comprising: a first amide group having a nitrogen atom and a carbonyl group; a second amide group tethered directly or indirectly through an organic group at the carbonyl group of the first amide group; and two organic groups terminated with a hydroxyl group attached to the nitrogen atom of the first amide group.

BRIEF DESCRIPTION OF THE DRAWINGS

FIG. 2 provides structures of thermoresponsive polymers. Synthetic polymers, such as those based on hydrophilic monomers like hydroxybutylvinylether (HOBVE), 2-hydroxyisopropylacrylamide (HIPAM), 2-carboxyisopropylacrylamide (CIPAM), and glycidyl methacrylate (GMA) have been shown to form thermoresponsive coacervate droplets.

showing coacervate droplets at room temperature under brightfield filter. For scale, the bar is 20 μm.

Figures 5A, 5B, 5C:
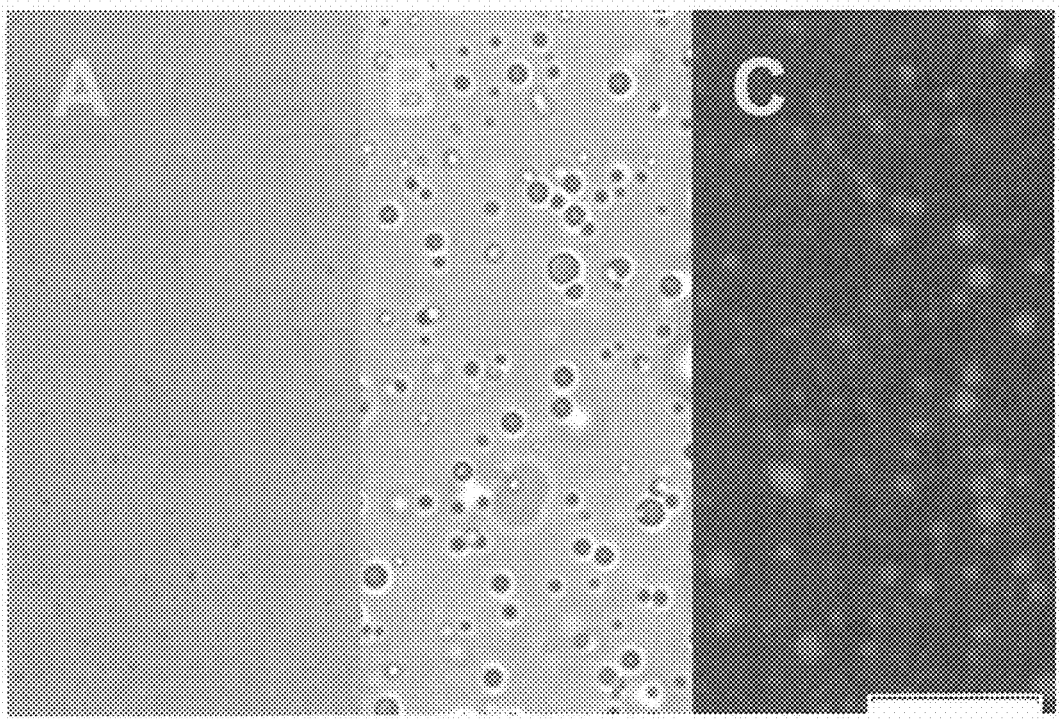
FIG. 5A provides an optical micrograph (0.5 wt %, 40× magnification) of TR-DEPE (Mn=55 kDa, Tcp=11.9° C.)

FIG. 5B provides an optical micrograph (0.5 wt %, 40× magnification) of TR-DEPE (Mn=55 kDa, Tcp=11.9° C.) showing coacervate droplets at room temperature under after introduction of Nile Red under brightfield. For scale, the bar is 20 μm.

FIG. 5C provides an optical micrograph (0.5 wt %, 40× magnification) of TR-DEPE (Mn=55 kDa, Tcp=11.9° C.) showing coacervate droplets at room temperature under TRITC filters. For scale, the bar is 20 μm.

Figure 6:
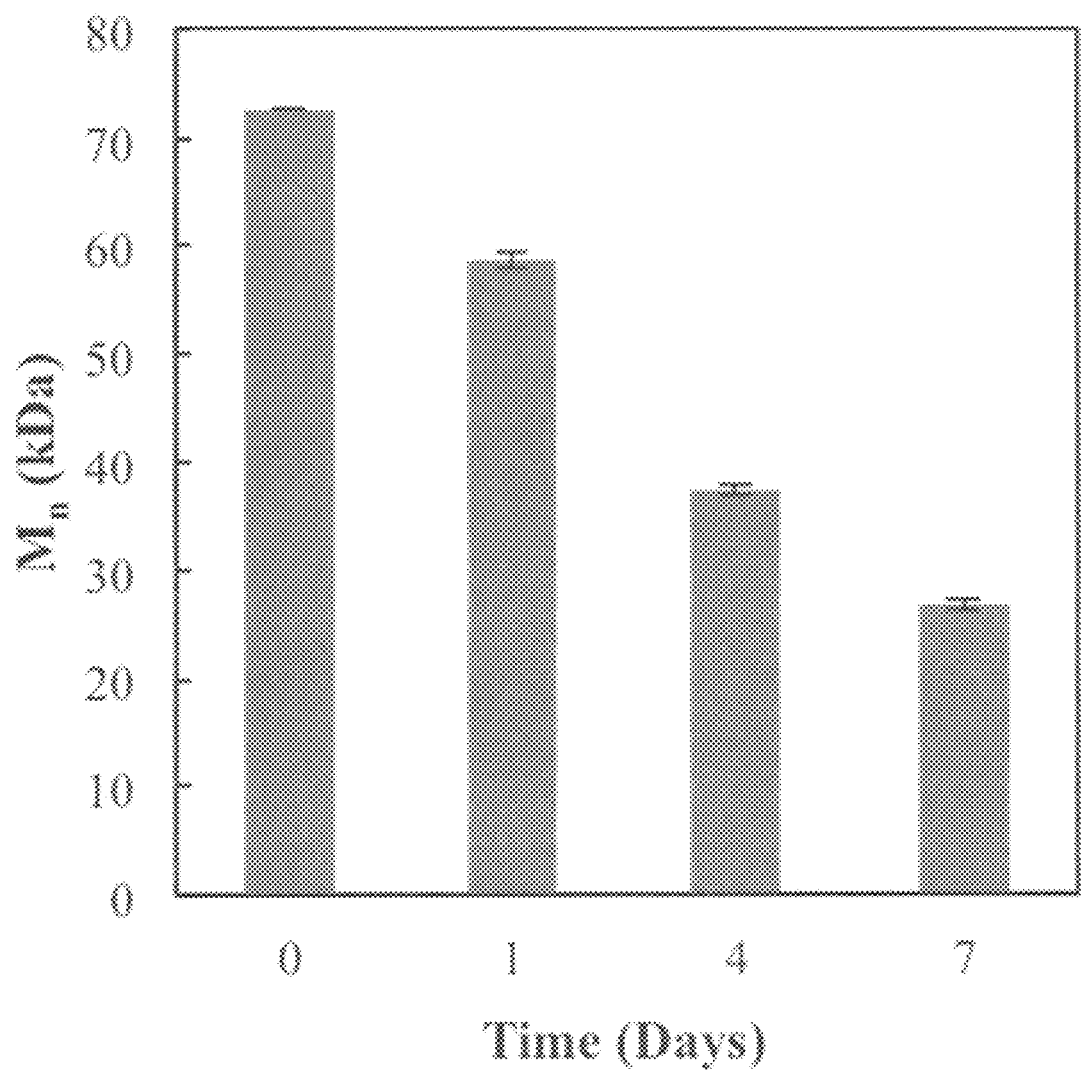

FIG. 6 provides a graph of the hydrolytic degradation of TR-DEPE over a period of 7 days; n=3.

Figure 7:
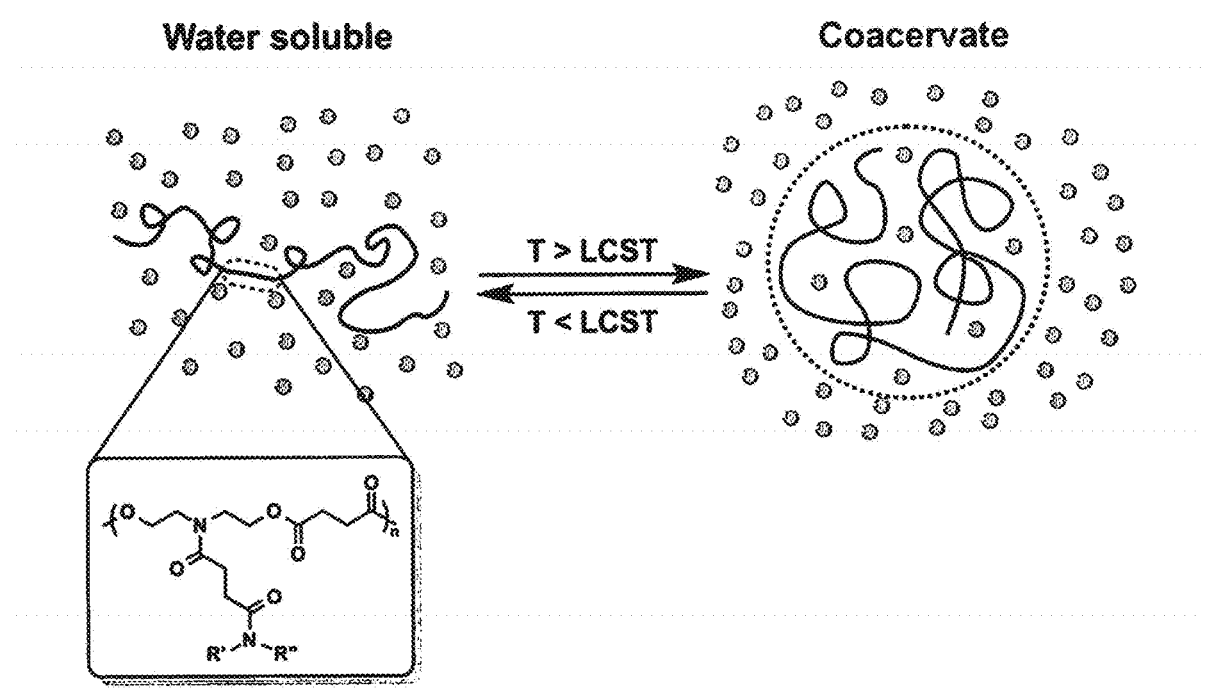

FIG. 7 provides a schematic for the thermally induced reversible hydrophobicity change of one or more embodiments, where the thermoresponsive polyester forms a coacervate.

DETAILED DESCRIPTION OF ILLUSTRATIVE EMBODIMENTS

In one or more embodiments a thermoresponsive polyester is provided. The thermoresponsive polyester may comprise a first amide group having a nitrogen atom and a carbonyl group; a second amide group tethered directly or indirectly through an organic group at the carbonyl group of the first amide group; and the nitrogen atom of the first amide group is part of the backbone of the polyester. It has been found that the thermoresponsive polyesters can undergo a thermally induced reversible hydrophobicity change. The thermoresponsive polyesters have a unique combination of properties not typical among other thermoresponsive polymers. Advantageously, the thermoresponsive polyesters may form a coacervate droplet at certain temperatures. The thermoresponsive polyesters are additionally biodegradable. Thermoresponsive polyesters may be used as agents for the purification of proteins and nucleic acids, as controlled delivery agents for sensitive physiologically active molecules, and as injectable scaffolds.

In one or more embodiments, thermoresponsive polyesters may be prepared from the polymerization of an amide functional diol compound. Those skilled in the art will recognize that a polyester may be prepared from a diol compound with copolymers containing carboxylic acid groups or ester groups using a polycondensation reaction. In one or more embodiments, a thermoresponsive polyester may be prepared using a carbodiimide-mediated polymerization.

The thermoresponsive polyesters may be prepared from an amide functional diol compound and at least one co-monomer. Suitable co-monomers include dicarboxylic acids, hydroxy acids, and diols. Suitable co-monomers are disclosed in WO 2013/130985, which is incorporated herein by reference in its entirety.

The thermoresponsive polyesters may be characterized by the units that derive from the monomers polymerized to prepare the polyester. In these or other embodiments, the derived units are the mer units that result from the monomers that have been reacted to form the polyester. For example, a thermoresponsive polyester may be prepared from an amide functional diol compound and a dicarboxylic acid. In these or other embodiments, the polyester may comprise units derived from an amide functional diol compound and units derived from a dicarboxylic acid. One or more embodiments may include units that derive from other co-monomers.

In one or more embodiments, the amide functional diol compound may comprise a first amide group having a nitrogen atom and a carbonyl group a second amide group tethered directly or indirectly through an organic group at the carbonyl group of the first amide group; and two organic groups terminated with a hydroxyl group attached to the nitrogen atom of the first amide group.

Those skilled in the art will recognize that an amide compound may be defined by the following formula:

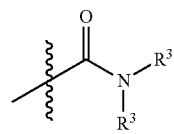

where each $R^3$ is individually a hydrogen atom or an organic group, or where both $R^3$ groups join to form an organic group In one or more embodiments the second amide group may selected from the group consisting of

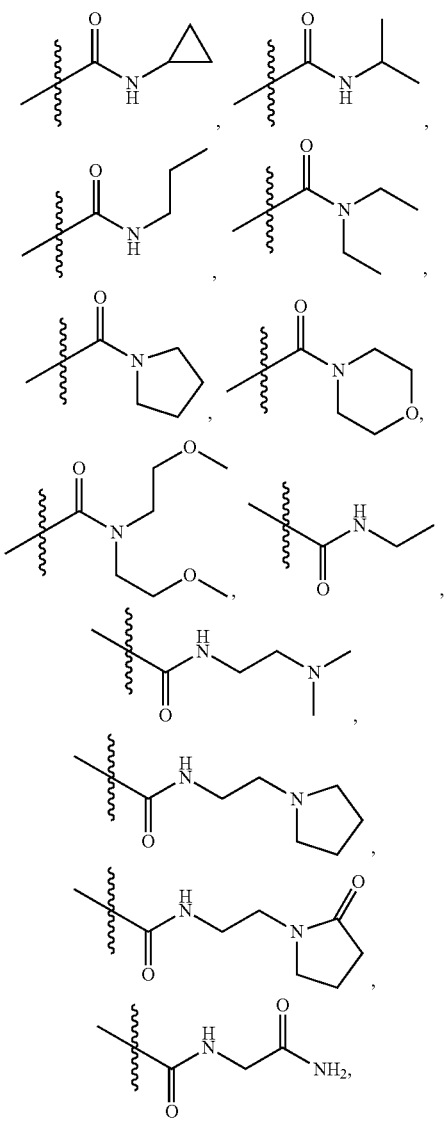

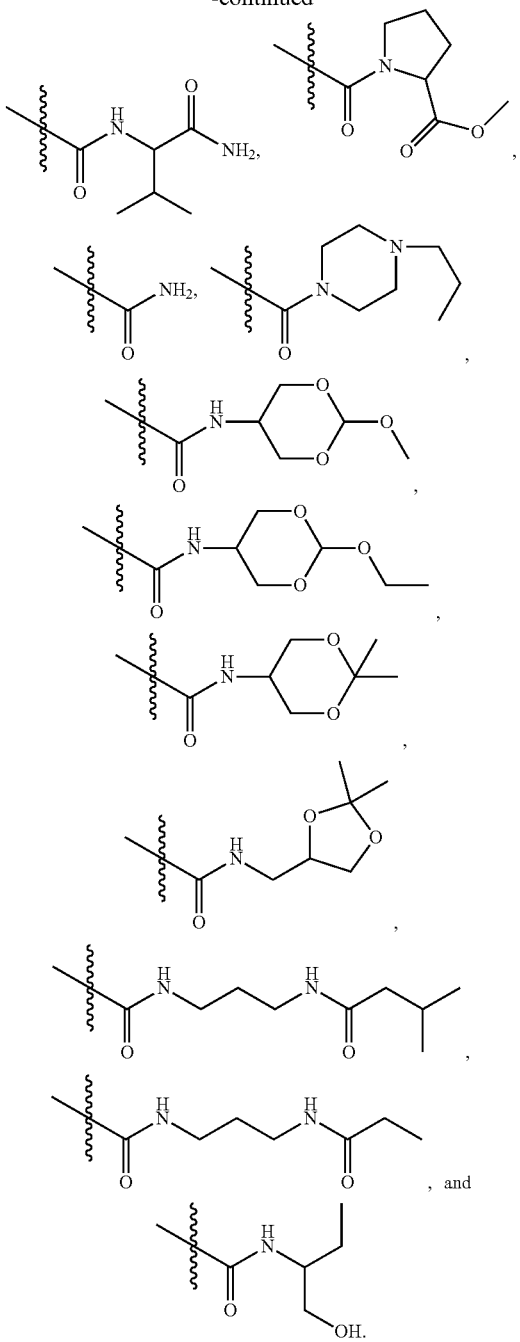

, and

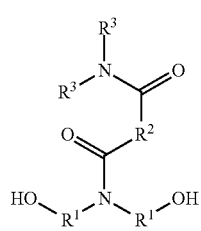

In one or where the amide functional diol compound may be defined by formula 1:

where each $R^1$ is individually a hydrocarbon group, $R^2$ is a hydrocarbon group, and each $R^3$ is individually a hydrogen atom or an organic group, or where both $R^3$ groups join to form an organic group.

In one or more embodiments, where each $R^1$ group and the $R^2$ group of formula 1 are hydrocarbon chains, the amide functional diol compound may be defined by formula 2:

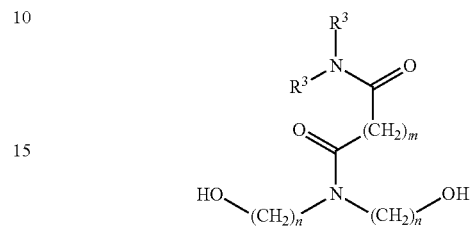

where each n is individually from 2 to 4 units, m is from 2 to 6 units, and each $R^3$ is individually a hydrogen atom or an organic group, or where both $R^3$ groups join to form an organic group.

In one or more embodiments, where the hydrocarbon chains of formula 2 are each two carbons long chains, the amide functional diol compound may be defined by formula 3:

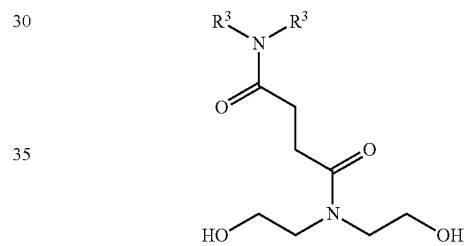

where each $R^3$ is individually a hydrogen atom or an organic group, or where both $R^3$ groups join to form an organic group.

In one or more embodiments, suitable organic groups include hydrocarbon groups or substituted hydrocarbon groups. Suitable hydrocarbon groups or substituted hydrocarbon groups may be linear, cyclic, or branched. The hydrocarbon groups or substituted hydrocarbon groups may include 1 to 10 carbon atoms. In one or more embodiments, hydrocarbon groups suitable for use as an $R^3$ group may include more than 10 carbon atoms. Substituted hydrocarbon groups include those hydrocarbons where a hydrogen or carbon atom has been replaced by heteroatom. Suitable heteroatoms include, but are not limited to, halogens, oxygen, sulfur, and nitrogen atoms.

Suitable dicarboxylic acids useful as copolymers may be defined by the formula 4:

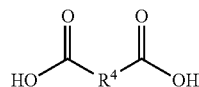

where $R^4$ is an organic group.

Advantageously, the organic group $R^4$ may be selected to tailor the properties of the thermoresponsive polyester. In one or more embodiments, the LCST may be tailored by adjusting the hydrophobicity of the organic group $R^4$. For example, the hydrophobicity may be adjusted by altering the chain length of $R^4$ or adding a functional group. In one or more embodiments, $R^4$ may be a hydrocarbon group with 1 to 10 carbon atoms. In other embodiments, $R^4$ may be a polyoxyethylene $(O-CH_2-CH_2)_n$ group. Suitable molecular weights of polyoxyethylene groups may be from 200 to 4000, in other embodiments 200 to 2000, and in still other embodiments 200 to 1000. In other embodiments, $R^4$ may include a functional group. In these embodiments, the dicarboxylic acids may be referred to as a functional dicarboxylic acids. In certain embodiments, were $R^4$ includes a functional group the functional group may be pendantly attached to the dicarboxylic acid. Functional groups may be added to alter the hydrophobicity or add a selectivity to the resultant thermoresponsive polyester. Specific examples of dicarboxylic acids with functional groups include glutamic acid, malic acid, tartaric acid etc., where the amine or hydroxyl group is protected prior to polymerization. Those skilled in the art will appreciate that these functional groups of the functional dicarboxylic acids may be protected. Suitable protecting groups include, but are not limited to Tetrahydropyranyl (THP), tert-butyldimethylsilyl (TBDMS), trimethylsilyl (TMS), and tert-Butoxy carbamate (Boc).

Suitable diols useful as copolymers may be defined by formula 5:

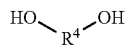

where $R^4$ is an organic group.

Similarly with the dicarboxylic acids, the organic group $R^4$ of the diol may be selected to tailor the properties of the thermoresponsive polyester such as hydrophocity and selectivity. In one or more embodiments, $R^4$ may be a hydrocarbon group with 1 to 10 carbon atoms. In other embodiments, $R^4$ may be a polyoxyethylene $(O-CH_2-CH_2)_n$ group. Suitable molecular weights of polyoxyethylene groups may be from 200 to 4000, in other embodiments 200 to 2000, and in still other embodiments 200 to 1000. In other embodiments, $R^4$ may include a functional group. In these embodiments, the diol may be referred to as a functional diol. In certain embodiments, were $R^4$ includes a functional group the functional group may be pendantly attached to the dicarboxylic acid.

In one or more embodiments, where the diol has a pendant functional group, the functional diol may be defined by formula 6:

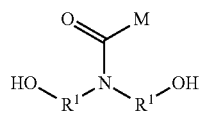

where M is a pendant functional group. Specific examples of functional groups suitable for use in a functional diol include, but are not limited to

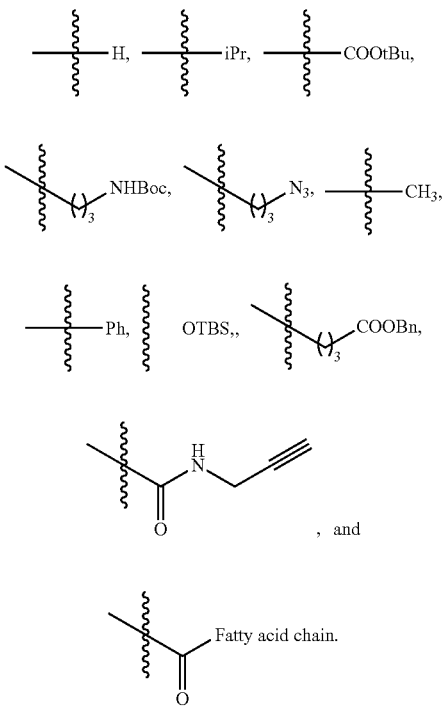

In one or more embodiments, the thermoresponsive polyester may comprise a first amide group having a nitrogen atom and a carbonyl group; a second amide group tethered directly or indirectly through an organic group at the carbonyl group of the first amide group, and the nitrogen atom of the first amide group is part of the backbone of the polyester. In these or other embodiments, the thermoresponsive polyester may include a unit defined by the formula I:

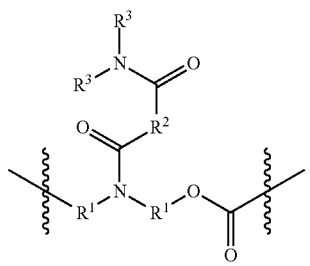

where each $R^1$ is individually a hydrocarbon group, $R^2$ is a hydrocarbon group, and each $R^3$ is individually a hydrogen atom or an organic group, or where both $R^3$ groups join to form an organic group. In certain embodiments, the thermoresponsive polyester includes about 20 to 600 units, in other embodiments about 30 to about 500 units, and in other embodiments about 40 to about 400 units defined by formula I.

As suggested above, a thermoresponsive polyester may be prepared by polymerizing an amide functional diol compound with a dicarboxylic acid. In these or other embodiments, the thermoresponsive polyester may include a unit defined by the formula II:

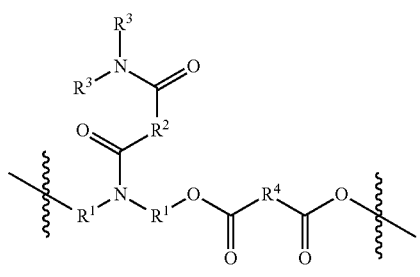

where each $R^1$ is individually a hydrocarbon group, $R^2$ is a hydrocarbon group, $R^4$ is an organic group, and each $R^3$ is individually a hydrogen atom or an organic group, or where both $R^3$ groups join to form an organic group. In certain embodiments, the thermoresponsive polyester includes about 20 to 600 units, in other embodiments about 30 to about 500 units, and in other embodiments about 40 to about 400 units defined by formula II.

As suggested above, a thermoresponsive polyester may be prepared by polymerizing an amide functional diol compound with a dicarboxylic acid and a functional diol compound. In these or other embodiments, the thermoresponsive polyester may include a unit defined by the formula III:

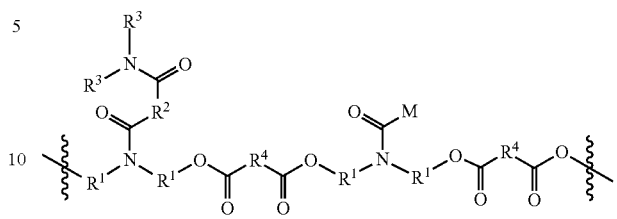

where each $R^1$ is individually a hydrocarbon group, $R^2$ is a hydrocarbon group, each $R^4$ is individually an organic group, M is a pendant functional group, and each $R^3$ is individually a hydrogen atom or an organic group, or where both $R^3$ groups join to form an organic group. In certain embodiments, the thermoresponsive polyester includes about 10 to 300 units, in other embodiments about 15 to about 250 units, and in other embodiments about 20 to about 200 units defined by formula III.

Specific examples of thermoresponsive polyesters include, but are not limited to:

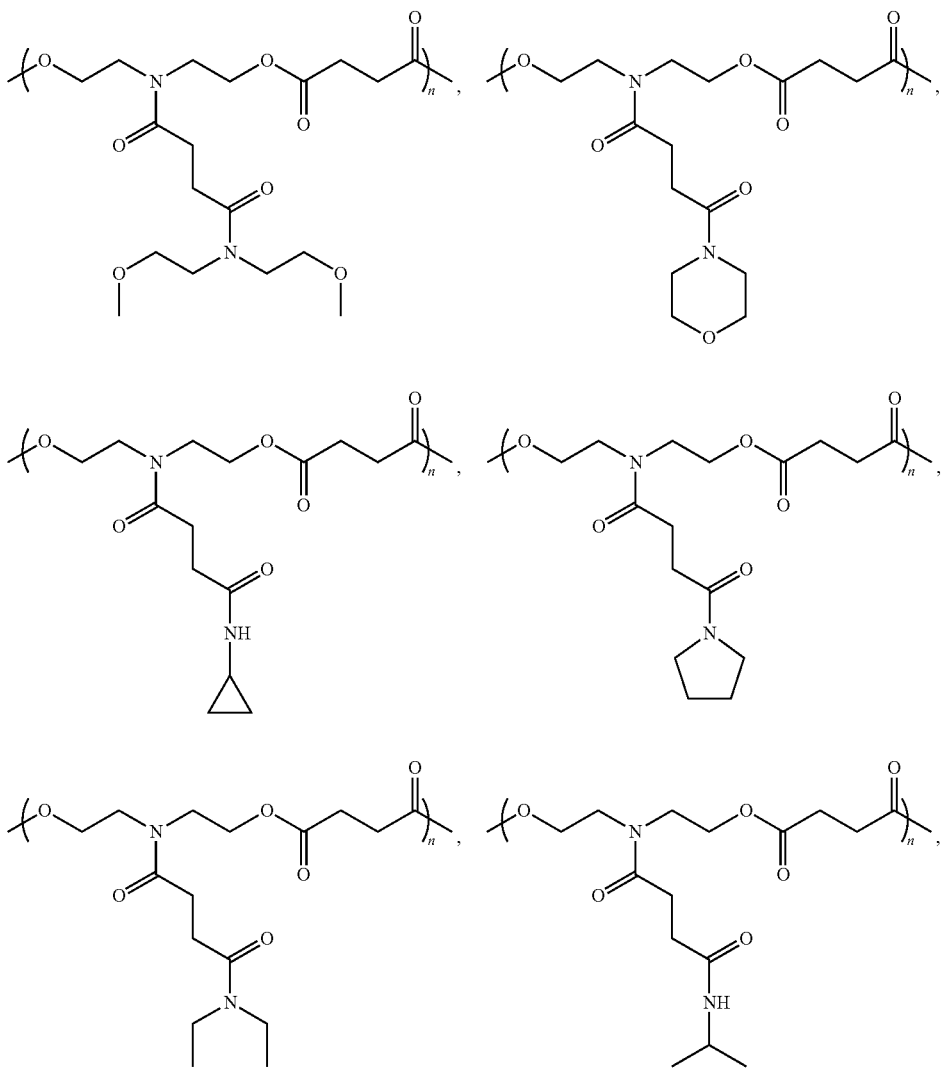

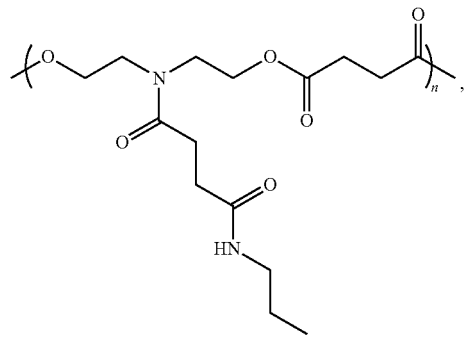
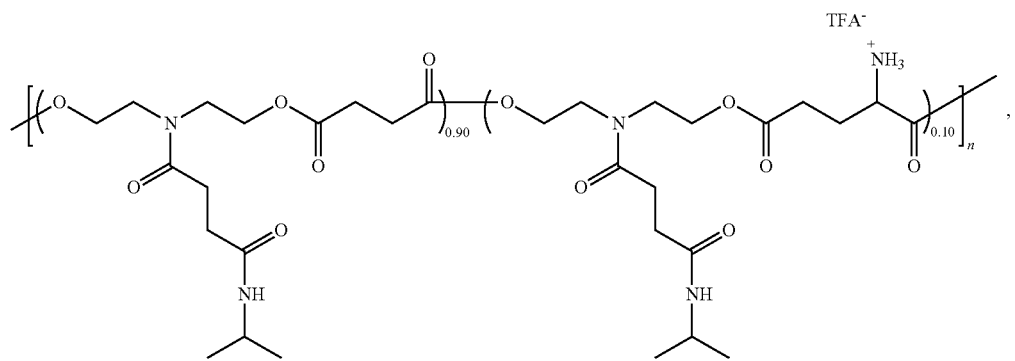
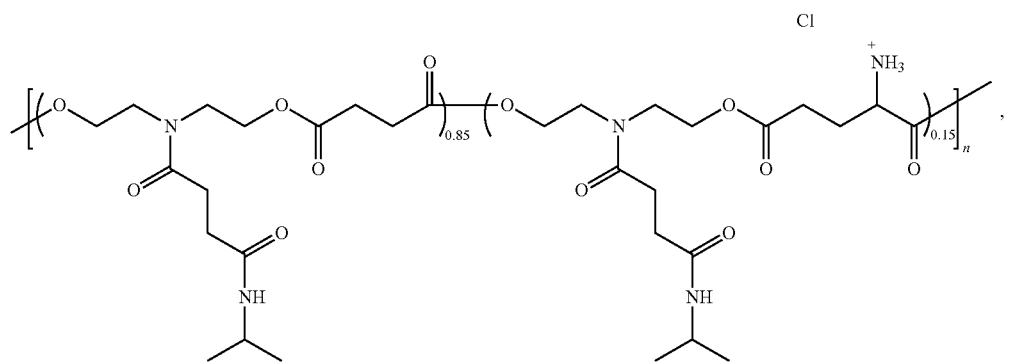
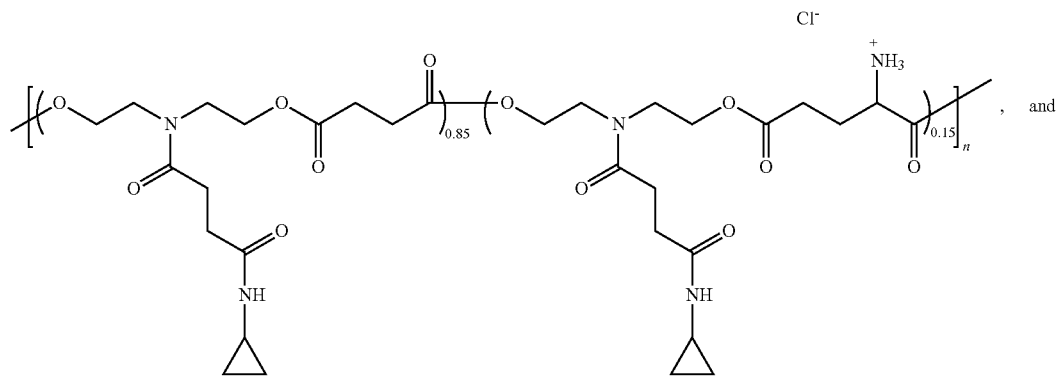

-continued

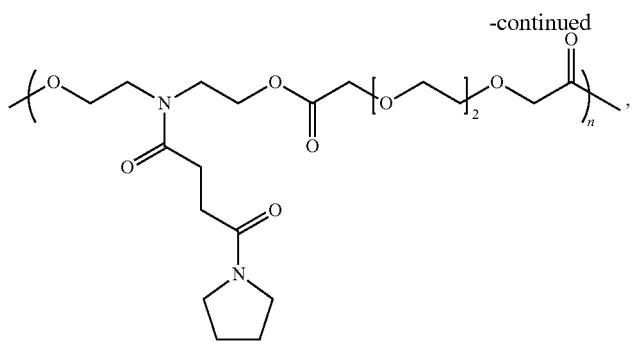

where each n is individually about 20 to 600 units in other embodiments about 30 to about 500 units, and in other embodiments about 40 to about 400 units The molecular weight of the thermoresponsive polyester may be determined through size exclusion chromatography. In one or more embodiments, the functionalized amide polymers are made to have a number average molecular weight from about 5,000 to about 200,000 g/mol. In one or more embodiments, the functionalized amide polymers are made to have a number average molecular weight from about 20,000 to about 160,000 g/mol. In one or more embodiments, the polydispersity of the thermoresponsive polyesters may range from about 1.1 to about 2.0.

In one or more embodiments, the thermoresponsive polyester may be characterized by an advantageous lower critical solution temperature (LCST), which may be measured using dynamic light scattering to determine the cloud point temperature for thermoresponsive polyester that form coacervates. Advantageously the LCST of the thermoresponsive polyester may be tuned by selecting different amide groups and by the selection of copolymers. In one or more embodiments, the thermoresponsive polyester is characterized by a LCST that is at least 5° C., in other embodiments at least 7° C., and in other embodiments at least 45° C. In these or other embodiments, the thermoresponsive polyester is characterized by a LCST that is at most 50° C., in other embodiments at most 90° C., and in other embodiments at most 95° C. In certain embodiments the thermoresponsive polyester may be characterized by a LCST that is from about 5° C. to about 95° C., in other embodiments from about 7° C. to about 90° C., and in other embodiments from about 45° C. to about 50° C.

As noted above the thermoresponsive polyester may form a coacervate in an aqueous solution. In one or more embodiments, an aqueous solution is a solution where the solvent is water. In other embodiments, an aqueous solution is a solution where the predominant solvent is water. In other embodiments, an aqueous solution is a solution where there is a sufficient amount of water present to allow the thermoresponsive polyester to form a coacervate. Aqueous solutions may also include, but are not limited to, biological systems, buffered systems such as phosphate buffered saline, saline, and serum.

Generally, coacervates may form at a temperature above the LCST. While not to wishing to be bound by any particular theory, it is believed that coacervates are formed when there is an incomplete dehydration of the water molecules surrounding the thermoresponsive polyester at a temperature above the LCST. Once formed, coacervates may coalesce into precipitated polymer phases when they are centrifuged or when allowed to settle. Coacervates are advantageous, because they may be used to encapsulate sensitive molecules without damaging the molecule or disrupting their function.

Molecules suitable for encapsulation include small molecules, oligomers, and macromolecules. Suitable small molecules for encapsulation include active pharmaceutical ingredients, fluorescent dyes, and imaging agents. Suitable oligomers for encapsulation include peptides, oligonuecleotides, and oligosaccharides. Suitable macromolecules for encapsulation include polysaccharides, and synthetic polymers.

In one or more embodiments, a thermoresponsive polyester may be used to purify an molecule in solution by mixing a thermoresponsive polyester into a solution containing a molecule to be purified, raising the temperature of the solution above the LCST of the thermoresponsive polymer to form a coacervate and encapsulate the molecule to be purified, and precipitating the coacervate. The coacervate may precipitate, for example, by centrifugal force. The solution may then be decanted from the precipitate and the coacervate may be cooled to release the molecule. In one or more embodiments, the thermoresponsive polyester may include a functional group with a suitable molecular specificity. In these or other embodiments, a functional group with molecular specificity may be imparted into the polymer by preparing a thermoresponsive polyester with a functional diol or a functional dicarboxylic acid. For example, in these or other embodiments, a thermoresponsive polyester may include a charged functional group to be selective for charged proteins. In other embodiments, a thermoresponsive polyester may include a hydrophilic functional group to be selective for water soluble proteins.

In one or more embodiments, a thermoresponsive polyester may be used to deliver a drug to a patient. In these or other embodiments, a molecule with therapeutic properties may be encapsulated in a coacervate with a thermoresponsive polyester with a LCST above body temperature. The coacervate is then delivered to a patient, where it becomes exposed to a temperature below the LCST and releases the molecule with therapeutic properties. In other embodiments, a molecule with therapeutic properties may be encapsulated in a coacervate with a thermoresponsive polyester with a LCST below body temperature. The coacervate is then delivered to a patient, where the thermoresponsive polyester biodegrades and releases the molecule with therapeutic properties.

In one or more embodiments, a thermoresponsive polyester may be used as an injectable scaffold. An injectable scaffold may be useful for tissue growth such as cartilaginous tissue. Suitable thermoresponsive polyesters for use as injectable scaffolds include those with an LCST below body temperature. In these or other embodiments, a highly concentrated solution of a thermoresponsive polyester that has been cooled to a temperature below the LCST of the thermoresponsive polyester may be delivered to a site within a patient. Once inside the patient, the thermoresponsive polyester forms a scaffold by rising to a temperature above the LCST of the thermoresponsive polyester and forming a coacervate. In these or other embodiments, the may be delivered along with a cell culture and other adjuvants for cell growth.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Synthesis and Characterization of Monomer and Polyesters

A set of five hydroxyethyl succinamide (HESA) monomers were synthesized. Despite the lower functional group density of the polyesters as compared to polyacrylamides, it was believed that the more hydrophilic pendant groups would impart temperature-sensitive solubility to the resultant thermoresponsive polyesters (TR-PE) as compared to the POx-like HEA polyesters. The desired amine was first reacted with ethyl succinyl chloride to produce the corresponding ethoxy amide in quantitative yields. A transamidation reaction in neat DEA afforded the pure HESA monomer after silica gel flash chromatography.

Figure 1:
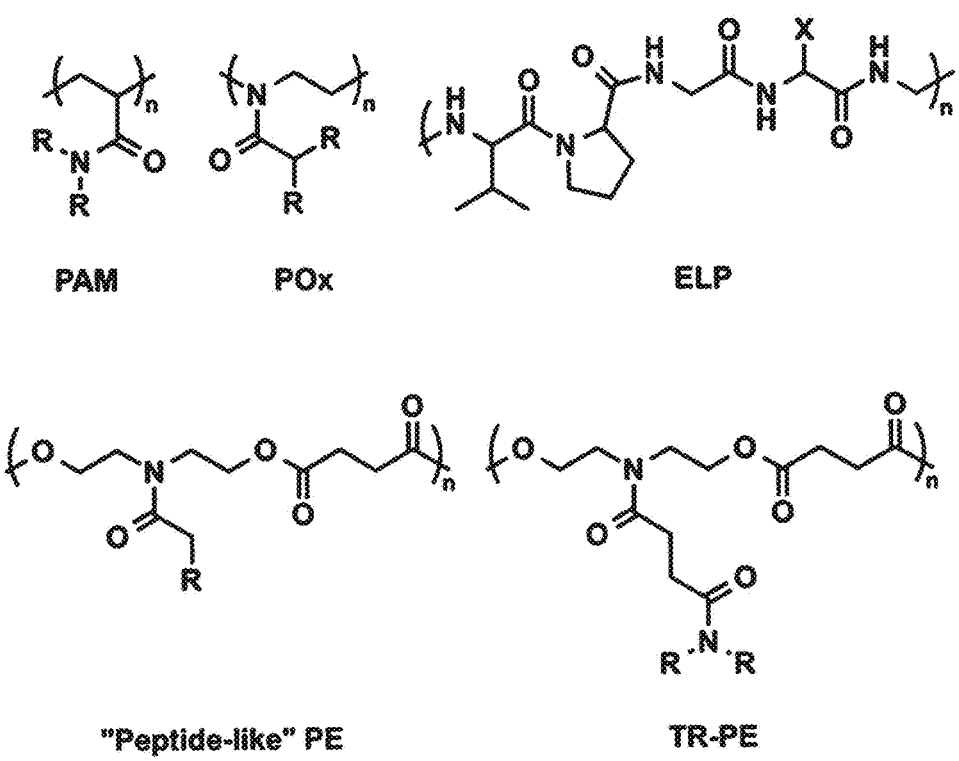
FIG. 1 provides the chemical structure of polyacrylamides (PAM), polyoxazolines (POx), elastin-like polypeptides (ELPs), "peptide-like" polyesters, and thermoresponsive polyesters.
Figure 3:
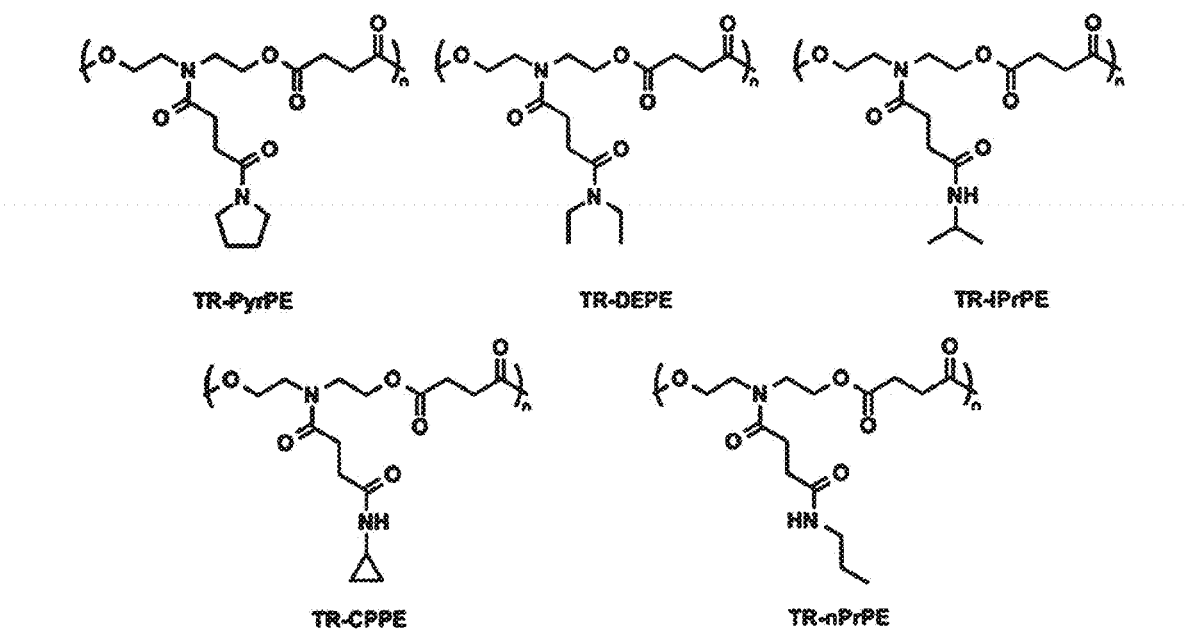
FIG. 3 provides structures of thermoresponsive polyesters.

HESA monomers were then polymerized using room temperature carbodiimide-mediated polyesterification. Owing to the similar solubilities of the monomers, polyesters, DPTS, and DIC urea byproducts in common solvents, purification by precipitation proved unsuccessful. Instead, pure TR-PEs were obtained by dialysis against MeOH at room temperature for 24 h and drying under reduced pressure (FIG. 3). The resultant polyesters were characterized by NMR, which proved the removal of DPTS and urea byproducts. Adjusting the stoichiometry of diol to diacid in the polymerization resulted in a variety of molecular weight TR-PEs that were analyzed via GPC.

Thermally Induced Phase Transitions.

Figure 4A:
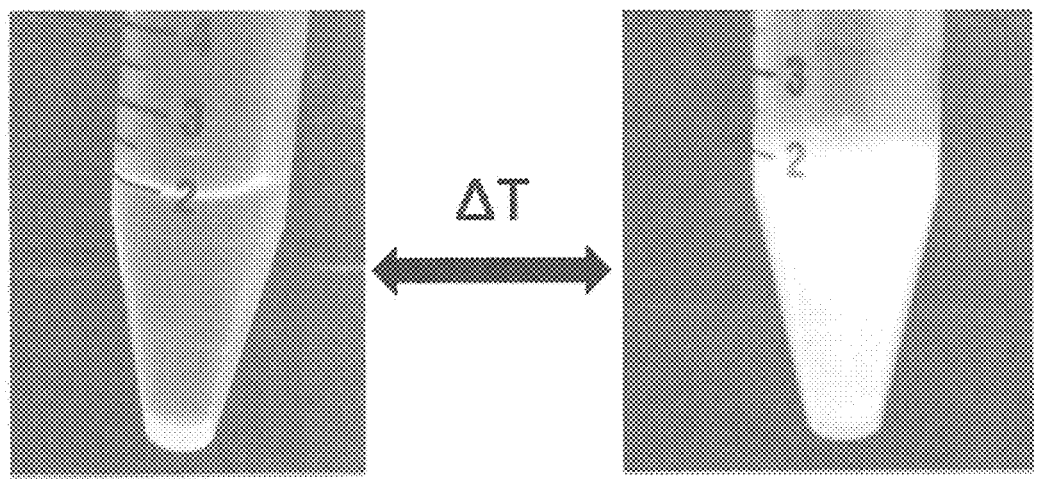
FIG. 4A provides images showing the reversible cloud point behavior of TR-PyrPE (Top, Tcp=15.8° C., 10 mg/mL).

Aqueous solutions (10.0 mg/mL) of TR-PEs were prepared by equilibrating the polyester in DI water overnight at 4° C. High molecular weight (~55 kDa) TR-iPrPE, TR-DEPE, and TR-PyrPE were water soluble at low temperatures and showed a rapid increase in turbidity upon being brought to room temperature (FIG. 4A). Cloudy solutions of these polyesters could be returned to their initial transparent state upon cooling. Despite their lower molecular weights (~25 kDa), TR-CPPE and TR-nPrPE were not completely soluble in aqueous conditions at 0° C.

Figure 4B:
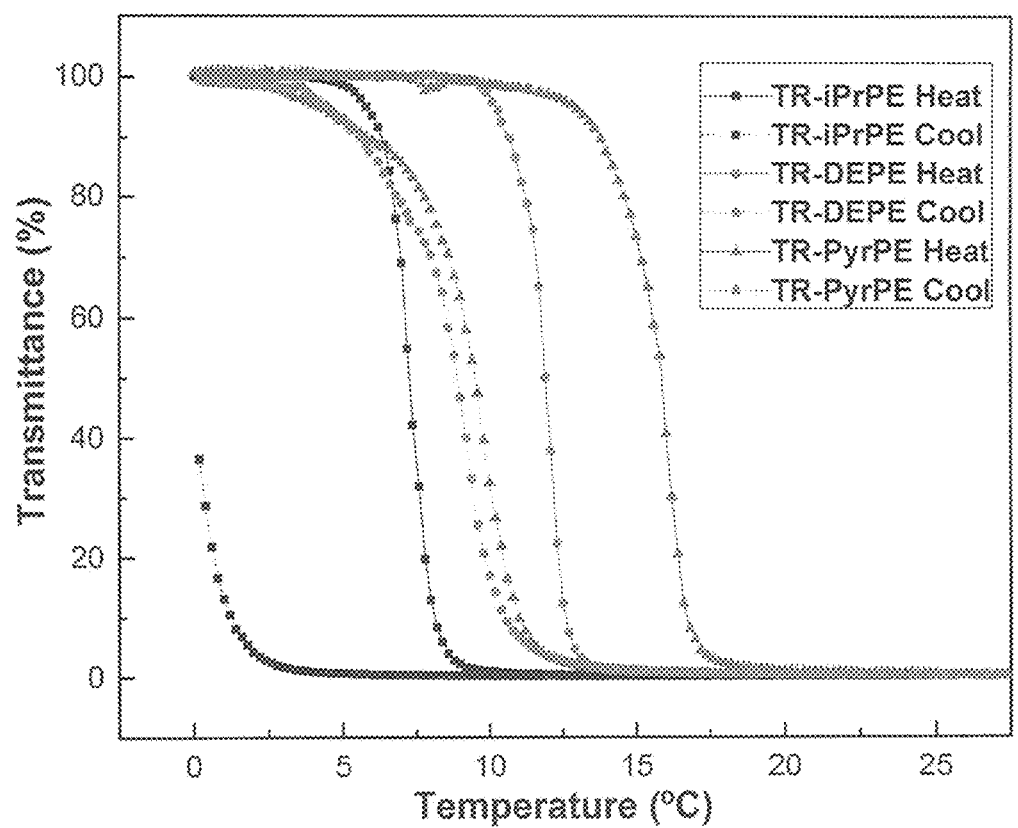
FIG. 4B. Temperature dependent transmittance of TR-iPrPE, TR-DEPE, and TR-PyrPE (Bottom, Mn~55 kDa, 10 mg/mL, 1° C./min) in DI water exhibiting clear hysteresis.

The thermoresponsivity of aqueous TR-PE solutions was probed using UV-Vis and $^1$H NMR. To minimize molecular weight influences, TR-PE polyesters of similar high molecular weight were chosen for analysis. As shown in FIG. 4B, a clear reversible $T_{cp}$ was observed for three TR-PEs of similar molecular weight: TR-iPrPE (7.8° C.), TR-DEPE (11.9° C.), and TR-PyrPE (15.8° C.). As hypothesized, the $T_{cp}$ was modulated by amide side chain identity. However, the $T_{cp}$ trend for TR-PEs did not seem to follow that for polyacrylamide (FIG. 2), as TR-CPPE was expected to have a $T_{cp}$ near that of TR-PyrPE but was instead insoluble. Similarly, TR-DEPE and TR-iPrPE were expected to have comparable $T_{cp}$ but instead showed a 4.1° C. difference. These differences will be discussed in further detail below. Compared to thermoresponsive polyacrylamides, the TR-PEs exhibit a more significant hysteresis with TR-iPrPE being unable to fully rehydrate within the experimental time frame. A small increase in hysteresis is commonly observed when intra- and intermolecular hydrogen bonds form in the dehydrated state making rehydration more difficult. Given the hydrogen bond donating secondary amide of TR-iPrPE and numerous hydrogen bond accepting oxygen and nitrogen atoms in the polyester, it is likely that such intra or intermolecular hydrogen bonds are influencing the significant hysteresis as compared to TR-DEPE and TR-PyrPE. It has been reported that the self-assembly of complex structures such as β-turns can increase hysteresis by up to 20° C. in the case of certain ELPs.

Scheme 1. Synthetic route for the preparation of polyesters$^a$

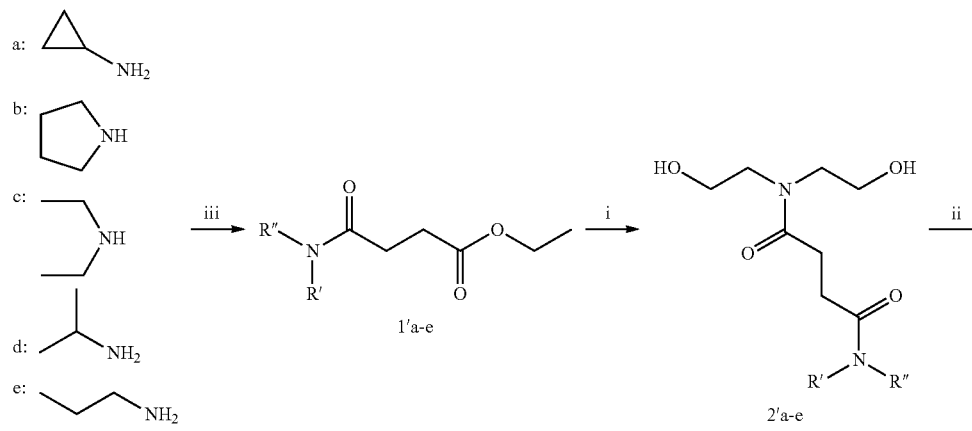

-continued

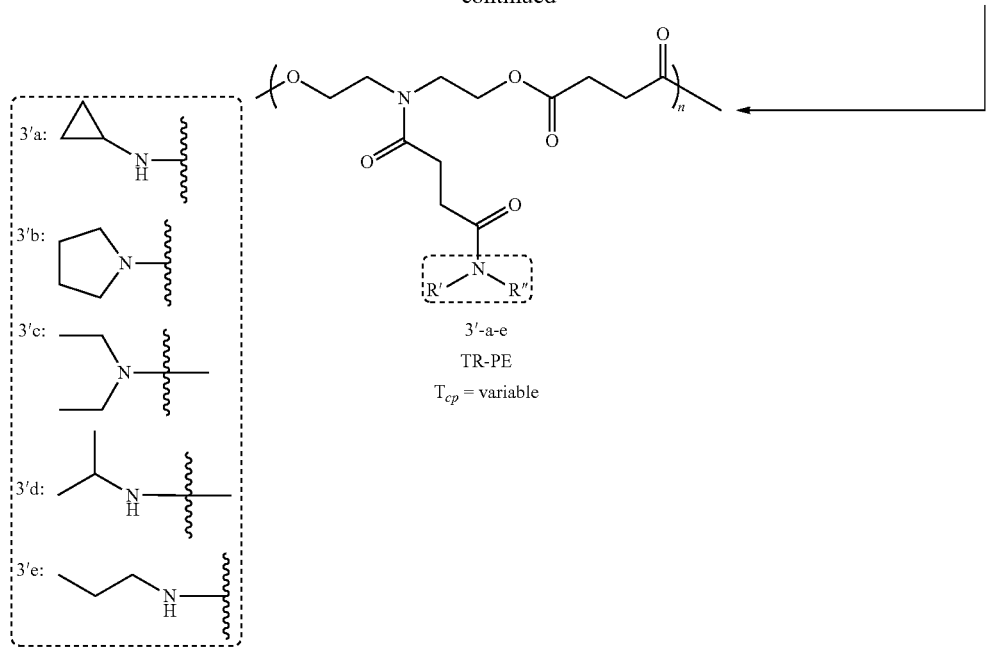

3'-a-e
TR-PE
$T_{cp}$ = variable

<sup>a</sup>Reagents and conditions:
(i) Diethanolamine, neat, 80° C., 16 h.
(ii) Succinic acid, DIC, DPTS, CH$_2$Cl$_2$, 0° C. to room temperature, 48 h.
(iii) Ethyl succinyl chloride, Et$_3$N, CH$_2$Cl$_2$, 0° C. to room temperature, 1 h.

Preliminary attempts at determining if the TR-PEs exhibit any ordered structures were carried out by analysis of dilute TR-PE solutions. However these studies did not show any distinguishing circular dichroism (CD) signals and the lack of any chiral center in the polyesters may preclude any ordered structures for these polyesters.

Variable temperature $^1$H NMR in D$_2$O was used to examine the change in polyester hydration with temperature. Above the $T_{cp}$ at 20° C., the peaks corresponding to the DEA backbone begin to decrease in intensity and shift from two to three peaks as dehydration occurs. Moreover, the pyrrolidinyl alkyl peaks are seen to decrease in intensity and transform. Unlike coil-globule polymers, no peaks are observed to completely disappear indicating partial instead of total dehydration and a coacervate-type response. Changes in peak intensity and shape are also observed above the $T_{cp}$ of TR-iPrPE and TR-DEPE.

It has been well established that the presence of an endothermic peak in a DSC measurement is one of the most accurate and robust methods for determining the LCST of thermoresponsive polymer solutions. The endothermic peak appears at the LCST when hydrogen bonds between structured water molecules and the polymer break, resulting in a large gain of entropy that compensates for the loss of entropy incurred by the dehydrated polymer. However, no endothermic peak was observed for any TR-PE solution even at high concentrations (150 mg/mL) despite showing a clear cloud point transition. This behavior is indicative of coacervate-type polymers, in which the partial dehydration of fewer structured waters leads to a reduced amount of entropy gained (relative to coil-globule polymers). The loss of entropy due to collapse of the polymer chain cannot be overcome by smaller entropy gained from partial dehydration of structured water molecules, leading to reduction or elimination of the endothermic peak. The absence of an endothermic peak in DSC strongly indicated that TR-PEs were coacervate-type polymers Effect of Polyester Concentration, Molecular Weight, and Cosolutes on Phase Transition.

In order to further explore the aqueous solution properties of the TR-PE system, UV-Vis was used to probe the effect of polyester concentration, molecular weight, and cosolutes on $T_{cp}$. As expected, increasing polyester concentration increases the polyester available to form coacervates and results in an earlier onset of $T_{cp}$ similar to what is seen for other thermoresponsive systems. Increasing the molecular weight of TR-PEs decreases their solubility, in turn logarithmically decreasing the $T_{cp}$. This behavior is similar to what is observed with more monodisperse ELPs. Increasing the concentration of hydrogen bond disrupting NaCl is well known to promote thermoresponsive polymer collapse ("salting out" effect) and was observed to decrease the $T_{cp}$ in a linear fashion. Conversely, increasing the amount of SDS surfactant, which stabilizes the hydrated polyester, was observed to raise the $T_{cp}$ in agreement with previous literature precedent. Furthermore, it was noted that higher concentrations of SDS were able to solubilize TR-CPPE and TR-nPrPE which allowed for a temperature response.

PNIPAM has been previously used as a model to investigate the mechanism of protein denaturation by urea. Despite numerous investigations, this mechanism is still not well understood. The addition of urea results in a decrease of PNIPAM's LCST, which is hypothesized to be the result of urea interacting bivalently with the polymer and stabilizing its dehydrated state via intra- and intermolecular hydrogen bonding. An opposite effect is observed for ELPs in which the LCST increases with urea concentration, as the hydrated state is made more stable. The current TR-PE system was observed to display a linear increase in Tcp with increasing urea content, similar to that of ELPs. The resultant increase in thermoresponsive solubility was also seen for TR-CPPE and TR-nPrPE. This behavior strongly indicates that despite the monomers being inspired by acrylamides, in solution TR-PEs appear to behave similar to ELPs. In the future, TR-PEs may provide a better model to understand the role of urea in protein denaturation.

Tuning Phase Transition Temperature Via Copolymerization.

As TR-PE homopolyesters displayed distinctive $T_{cp}$, it was believed that thermoresponsivity could be tuned by copolymerization of different monomers, similar to other thermoresponsive polyacrylamides, polyesters, polyphosphoesters, and polyamides.

It has been previously established that the hydrophobic/hydrophilic balance can be used to control the behavior of thermoresponsive polymers. Given that the random "peptide-like" copolyester composition as determined by NMR was statistically similar to the monomer feed, it was expected that the composition of TR-PEs could be reasonably controlled by the monomer feed as well, resulting in control over the $T_{cp}$. Statistically random TR-PEs of similar high molecular weights display $T_{cp}$ between that of their respective homopolyesters (Table 2), indicating that the temperature response can be tuned by monomer feed.

nessed in the $T_{cp}$ experiments, polymer coacervate concentration did not seem to correlate with the hydrophobicity of the amide, which will be discussed in more detail below. The size of TR-PE coacervate droplets was quantified using DLS.

In a representative CONTIN analysis of the DLS measurements of TR-DEPE, the onset of coacervate formation is observed above the $T_{cp}$. Coacervate droplets are shown to be relatively monodisperse and stable for at least 3 hours, making them potentially useful for a number of biomaterials applications such as controlled delivery of therapeutics. It should be noted that there is small difference between the onset of coacervate formation, as obtained from DLS measurements, and $T_{cp}$. This is primarily due the qualitative nature of $T_{cp}$ experiments, which measure macroscopic changes and are affected by conditions such as concentration and heating rate. The results of DLS analysis show that the higher the $T_{cp}$ and coacervate water concentration, the greater the size of the resulting coacervate droplets (Table 1). Coacervates droplets of TR-iPrPE ($T_{cp}$=7.8° C.) begin at 100 nm, while those of TR-PyrPE ($T_{cp}$=15.8° C.) show an initial size of 220 nm. Based on the $T_{cp}$ and coacervate data, it seems that the type of amide present on the TR-PE side chain plays a greater effect on the solution properties than

TABLE 1

Characterization of TR-PEs

| Polyester | $M_n{}^a$ (kDa) | $M_w{}^a$ (kDa) | Đ$^a$ | $T_g{}^b$ (° C.) | $T_{cp}{}^c$ (° C.) | $T_{cp}$ PAM$^d$ (° C.) | Coacervate [Polyester] (%)$^e$ | Coacervate [Polyester] (mg/mL)$^e$ | Coacervate droplet $R_h$ (nm)$^f$ |
|---|---|---|---|---|---|---|---|---|---|
| TR-CPPE | 25.5 | 42.4 | 1.6 | 13.8 | N/A | 53[35] | 64.6 | 1830 | N/A |
| TR-nPrPE | 29.1 | 43.9 | 1.5 | 4.8 | N/A | 10[36] | 65.4 | 1890 | N/A |
| TR-iPrPE | 56.5 | 88.5 | 1.6 | 10.0 | 7.8 | 32[37] | 61.4 | 1590 | 102 |
| TR-DEPE | 56.5 | 87.6 | 1.5 | −4.2 | 11.9 | 33[38] | 57.3 | 1340 | 118 |
| TR-PyrPE | 54.2 | 86.6 | 1.5 | 0.2 | 15.8 | 51[39] | 44.2 | 792 | 226 |

$^a$Determined by DMF GPC relative to PMMA standards.
$^b$Determined by DSC.
$^c$Defined as 50% transmission during temperature controlled UV-Vis analysis.
$^d$Corresponding values of thermoresponsive polyacrylamides.
$^e$Average of three measurements.
$^f$Determined using temperature controlled DLS analysis.

TABLE 2

Characterization of TR-PE copolyesters

| Monomer feed (iPr:Pyr) | Polyester composition$^a$ (NIP:Pyr) | Mn$^b$ (kDa) | Đ$^b$ | CP$^c$ (° C.) |
|---|---|---|---|---|
| 100:0 | 100:0 | 56.6 | 1.6 | 7.2 |
| 75:25 | 71:29 | 52.2 | 1.4 | 7.9 |
| 50:50 | 48:52 | 56.0 | 1.4 | 9.5 |
| 25:75 | 27:73 | 55.0 | 1.4 | 13.1 |
| 0:100 | 0:100 | 54.2 | 1.5 | 15.8 |

$^a$Determined by $^1$H NMR.
$^b$Determined by DMF GPC relative to PMMA standards.
$^c$Defined as 50% transmission during temperature controlled UV-Vis analysis.

Coacervate Analysis.

Upon being left at room temperature overnight, the turbid aqueous solutions of TR-iPrPE, TR-DEPE, and TR-PyrPE were observed to phase separate into a polymer-deficient aqueous phase and a viscous polymer-rich coacervate phase. As seen in FIG. 5A, optical microscopy of the turbid solutions showed sub-micron sized coacervate droplets. Centrifugation of the turbid solutions allowed for rapid coalescence of the coacervate droplets and analysis of the polyester concentration (Table 1). Following the trend witoriginally hypothesized. For all three secondary amide based TR-PEs, the $T_{cp}$ is much lower than would be expected if only hydrophilicity was taken into account. The tertiary amide based TR-PEs show better solubility, higher coacervate water content, and less hysteresis. This difference is likely due to the intra- and intermolecular hydrogen bonding available to the secondary amide side chain (a hydrogen bond donor and acceptor) and the numerous hydrogen bond accepting oxygen and nitrogen atoms per repeat unit as compared to the tertiary amide side chains (only a hydrogen bond acceptor). As previously discussed, such hydrogen bonding is known to increase the hysteresis of thermoresponsive polymers, and makes the re-solvation of the polymers less favorable. Our lab is currently studying other amide side chains in order to further investigate this hypothesis.

Nile Red Separation.

In order to show the feasibility of TR-PE coacervates for the thermally induced encapsulation of desirable compounds, Nile Red was used as a model compound. Nile Red is a hydrophobic dye with limited water solubility. A drop of 50 mM Nile Red in DMSO was added to a solution of TR-DEPE, which was quickly brought to room temperature. Upon coacervation and centrifugation, the purple dye-rich coacervate phase is easily observable. In contrast, no such behavior was observed when an aliquot of Nile Red was added to a blank solution. As seen in FIG. 5, the addition of Nile Red caused only the Nile Red swollen coacervates to emit a red fluorescence indicating successful incorporation of the dye.

Degradation Behavior.

The polyester backbone of the TR-PE system possesses inherent hydrolytic degradability. This is a significant advantage for numerous biomedical applications as compared to nondegradable thermoresponsive polymers such as PNIPAM or the enzymatically cleavable backbone of poly (amino acids) like ELPs. As a model study, the degradation of TR-DEPE was monitored at 37° C. and the decrease in $M_n$ is shown in FIG. 6. Over a period of 7 days, TR-DEPE degraded from 72.7 kDa to 26.7 kDa, a 63% $M_n$ loss. This is comparable to the degradation of the more hydrophobic p(mAla) "peptide-like" polyester, which degraded from 63.3 kDa to 41.4 kDa (a 35% $M_n$ loss) over the same 7 day period, as well as for the degradation of thermoresponsive poly (MEMO/ME$_2$MO-alt-SA) polyesters. Based on this evidence, it is reasonable to expect that that the four other TR-PEs will exhibit similar degradation trends. It is likely that the formation of a polymer-rich coacervate phase reduced the rate of ester bond hydrolysis, resulting in a slower degradation than would occur with a completely soluble polyester.

Experimental Section

Materials. Succinic acid (99%), ethyl succinyl chloride (98%), isopropylamine (99%), pyrrolidine (99%), propylamine (98%), cyclopropylamine (99%), triethylamine (Et$_3$N, 98%), diethanolamine (DEA, 99%), sodium chloride (NaCl, 99%), urea (98%), and sodium dodecyl sulfate (SDS, 98%) were purchased from Acros Organic and used as received. N,N'-diisopropylcarbodiimide (DIC, 99%) was purchased from Oakwood Chemical and used as received. 4-(dimethylamino)-pyridinium-4-toluene sulfonate (DPTS) was prepared according to literature methods. Reagent grade dichloromethane (CH$_2$Cl$_2$) was purchased from Thermo Fisher Scientific and dried by distilling over anhydrous CaH$_2$. Reagent grade tetrahydrofuran (THF) and methanol (MeOH) were used as received from Thermo Fisher Scientific. Silica gel (40-63 μm, 230×400 mesh) for flash chromatography was purchased from Sorbent Technologies, Inc. Dialysis tubing (regenerated cellulose, MWCO 3500 Da) was obtained from Thermo Fisher Scientific. Deionized water was used to prepare polyester solutions unless otherwise stated.

Characterization. $^1$H and $^{13}$C NMR spectra in CDCl$_3$ of the monomers and polyesters were recorded on either a Varian Mercury 300 MHz or 500 MHz spectrometer. Chemical shifts were recorded in ppm (δ) relative to solvent signals. Variable temperature $^1$H NMR spectra in D$_2$O were recorded on a Varian INOVA 400 MHz spectrometer with 15 minute equilibrations at each temperature. Glass transition temperatures (T$_g$) of the polyesters were determined using a TA Q2000 DSC with a liquid N$_2$ cooling unit and a heating/cooling rate of 10° C./min. Polyester molecular weights were analyzed on a TOSOH EcoSec HLC-8320 GPC equipped with a refractive index detector (RI) and UV detector. Separation occurred over two PSS Gram Analytical GPC Columns in series using 25 mM LiBr in DMF as eluent at a flow rate of 0.8 mL/min. The column and detector temperatures were maintained at 50° C. Molecular weights were obtained relative to PMMA standards using the RI signal.

Synthesis of HEA Monomers. As a representative example, methyl butyrate (5.00 mL, 43.9 mmol, 1 eq.) and DEA (9.23 g, 87.8 mmol, 2 eq.) were added to a round bottom flask equipped with a magnetic stir bar and heated at 80° C. overnight. After removing displaced MeOH under reduced pressure, the crude compound was analyzed via TLC (10% MeOH in DCM, ninhydrin). The product was observed at $R_f$~0.45 while unreacted DEA remained at $R_f$~0.05. The crude mixture was purified via silica gel flash chromatography (15% MeOH in CH$_2$Cl$_2$). The product was dried under reduced pressure to afford pure 1a (5.25 g, 30.0 mmol, 65%). The 1a monomer was characterized via NMR and IR.

Synthesis of HESA Monomers. As a representative example, pyrrolidine (3.0 mL, 36.5 mmol, 1 eq.) and Et$_3$N (5.20 mL, 37.3 mmol, 1.02 eq.) were dissolved in dry CH$_2$Cl$_2$ (40.0 mL) into a round bottom flask equipped with a magnetic stir bar. The reaction was cooled to 0° C. and purged with nitrogen for 15 min. Ethyl succinyl chloride (5.20 mL, 36.5 mmol, 1 eq.) was added dropwise and the reaction turned opaque white. The reaction was brought to room temperature and allowed to stir for 1 h under nitrogen. The solution was then added to DI water and extracted (3×40.0 mL CH$_2$Cl$_2$). The product was dried over MgSO$_4$, filtered, and concentrated under reduced pressure to afford pure 4a (6.98 g, 35.1 mmol, 96%). In a round bottom flask equipped with a magnetic stir bar 4a (6.73 g, 33.8 mmol, 1 eq.) and DEA (7.10 g, 67.5 mmol, 2 eq.) were added and allowed to heat at 80° C. overnight while stirring. After removing the displaced EtOH under reduced pressure, the crude compound was analyzed via TLC (15% MeOH in DCM, ninhydrin). A small amount of unreacted ethoxy amide ($R_f$~0.56) was observed along with the desired compound ($R_f$~0.40). The crude mixture was purified via silica gel flash chromatography (10-20% MeOH in CH$_2$Cl$_2$). The product was dried under reduced pressure to afford pure HESA monomer 4b (3.42 g, 13.2 mmol, 40%). The HESA monomer was characterized via NMR and IR.

Polymerization of Monomers. As a representative example, in a round bottom flask equipped with a magnetic stir bar, 3b (1.25 g, 4.85 mmol, 1 equiv.), succinic acid (573 mg, 4.85 mmol, 1 equiv.), and DPTS (570 mg, 1.94 mmol, 0.4 equiv.) were dissolved in dry CH$_2$Cl$_2$ (4.5 mL, 1.0 mL/100 mmol COOH) and purged with nitrogen for 15 minutes while stirring. This mixture was then briefly heated to homogenize the solution. The reaction was cooled to 0° C. and DIC (2.28 mL, 14.6 mmol, 3 eq.) was added dropwise via syringe. The reaction was allowed to come to room temperature and stirred for 24-48 h under nitrogen. The HEA polyesters 1b and 2b were purified by precipitation into a stirred solution of cold MeOH. Since the HESA monomers, polyesters, DPTS, and DIC urea byproducts all displayed similar solubilities in common organic solvents, 4c was purified via dialysis against MeOH for 24 h with solvent changes at 3 h, 6 h, and 16 h. The dialysis mixture was dried under vacuum to obtain pure 4c polyester as a white amorphous solid. The 4c polyester was characterized by GPC and NMR.

Coacervate Analysis. Optical microscopy was carried out on an Olympus IX81 Motorized Inverted Microscope using either Brightfield or TRITC channel filters. To image the coacervate droplets, aqueous polyester solutions (5.0 mg/mL) were brought to room temperature for 5 minutes and immediately imaged on glass slides. To probe coacervation polyester concentration, aqueous polyester solutions (15 mg/mL) were prepared and left at 4° C. overnight. The solutions were then moved to a static 37° C. incubator for 2 h. Incubated samples were centrifuged at 3600 RPM for 5 minutes to achieve rapid phase separation. The polyester-dilute supernatant was then carefully removed with a glass pipette leaving the polyester-rich coacervate phase at the bottom of the vial. The resulting polyester complex was then weighed and lyophilized. The coacervate polyester concentration was determined using the ratio of the dried polyester to the weight of the coacervate as the average of three separate samples.

Cloud Point Measurements. Turbidity measurements were carried out on a Shimadzu UV-1800 UV-VIS spectrophotometer equipped with a Shimadzu S-1700 thermoelectric single cell holder in a 1 cm quartz cell. Deionized water was used as a reference. Polyester solutions (10.0 mg/mL unless otherwise noted) were prepared in DI water and left at 4° C. overnight to ensure complete dissolution and equilibration. Solutions were equilibrated at 0° C. or 5° C. until no change in transmittance was observed. Transmittance was recorded as a function of temperature at 1° C./min at a fixed wavelength (350 nm). $T_{cp}$ was defined as the temperature at which the transmittance was 50%.

Light Scattering. Dynamic light scattering (DLS) measurements of the homopolyester aqueous solutions (0.5 mg/mL) were performed on a Brookhaven light scattering spectrometer (BI-200SM) equipped with a temperature controlled solid state laser ($\lambda$=532 nm). All DLS measurements were obtained at 90° scattering angle. An intensity-intensity time correlation function was measured by means of a multichannel digital correlator, which was then processed using the CONTIN method to obtain the average hydrodynamic radius of the particles in solution. The solutions were filtered through a 0.45 μm PVDF filter into glass vials and equilibrated for 30 minutes at each temperature prior to measurements.

Degradation Analysis. Aqueous polyester solutions (10.0 mg/mL in DI water) were placed in a static 37° C. incubator and removed at various time points. The polyester-dilute supernatant was then carefully removed with a glass pipette leaving the polyester-rich coacervate phase at the bottom of the vial. The resulting coacervate was rinsed with DI water, and lyophilized. The molecular weight of the dried coacervate was analyzed via GPC.

What is claimed is:

1. A thermoresponsive polyester comprising:
   a first amide group having a nitrogen atom and a carbonyl group;
   a second amide group tethered directly or indirectly through an organic group at the carbonyl group of the first amide group;
   where the nitrogen atom of the first amide group is part of the backbone of the polyester; and
   the second amide group is selected from the group consisting of

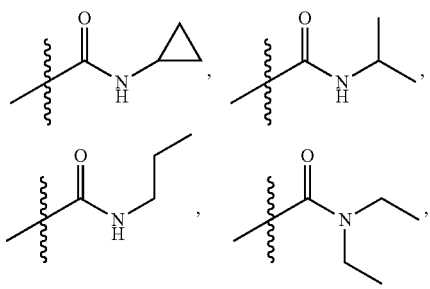

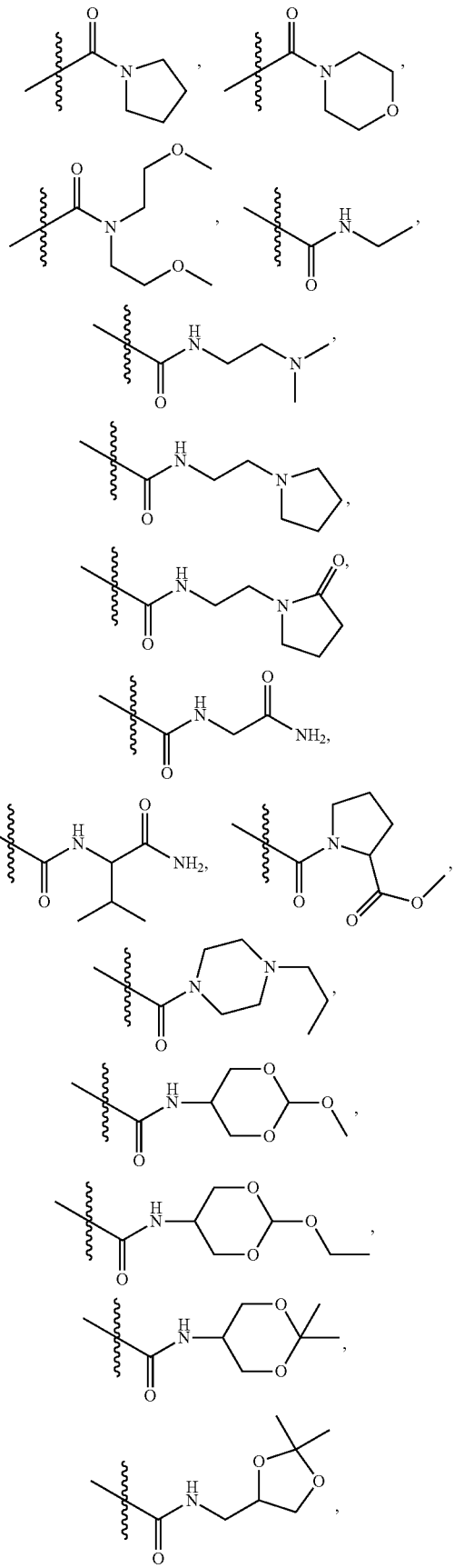

-continued

-continued

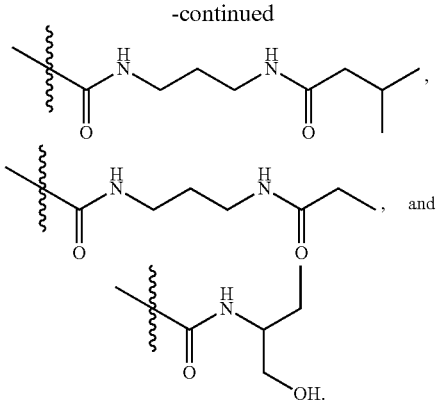

2. The thermoresponsive polyester of claim 1, where the thermoresponsive polyester includes a unit defined by the formula

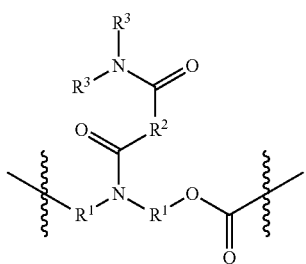

where each $R^1$ is individually a hydrocarbon group, $R^2$ is a hydrocarbon group, and both $R^3$ groups are part the second amide group, and is selected from the group consisting of

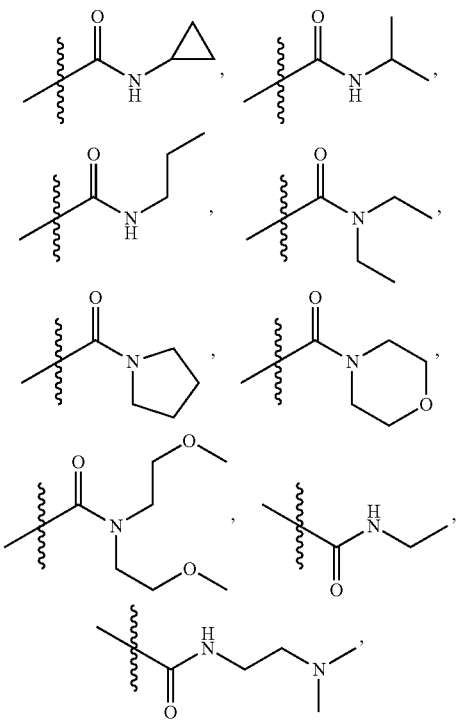

-continued

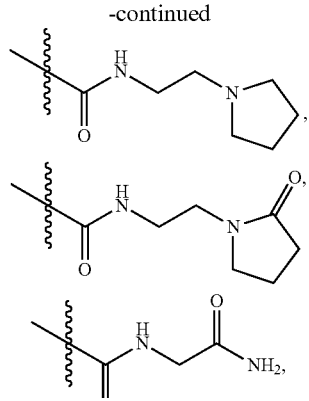

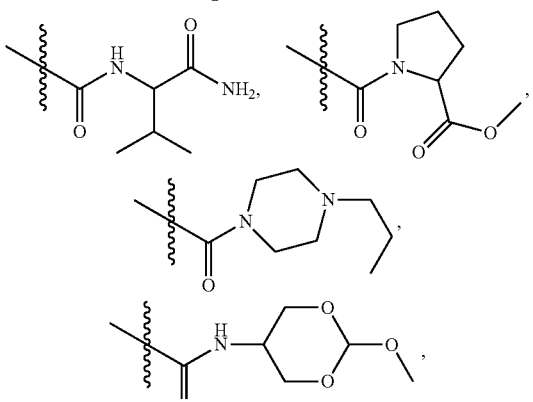

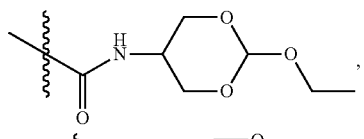

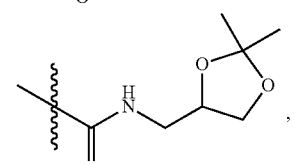

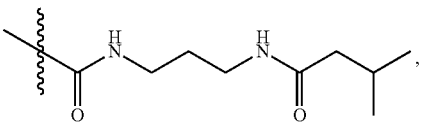

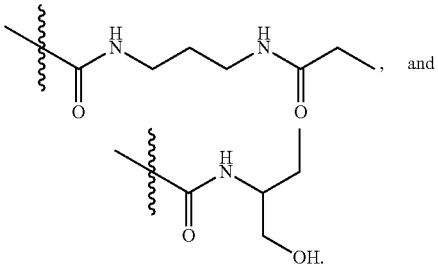

3. The thermoresponsive polyester of claim 1, where the thermoresponsive polyester includes a unit defined by the formula

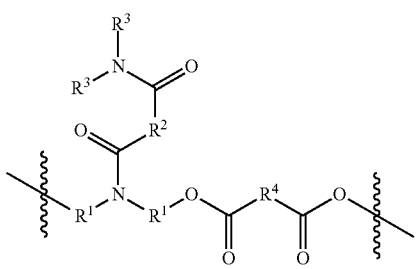

where each $R^1$ is individually a hydrocarbon group, $R^2$ is a hydrocarbon group, $R^4$ is an organic group, and both $R^3$ groups are part the second amide group, and is selected from the group consisting of

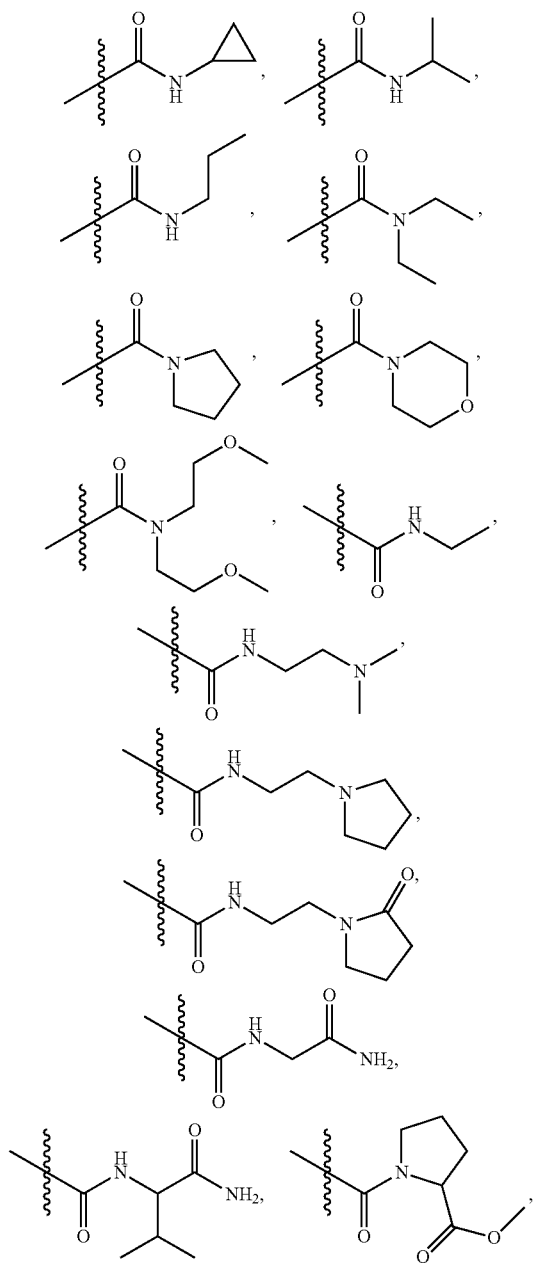

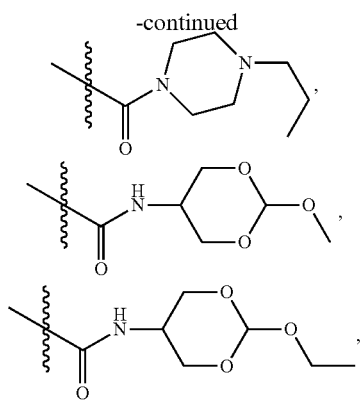

4. The thermoresponsive polyester of claim 3, where $R^4$ is a hydrocarbon group with 1 to 10 carbon atoms.

5. The thermoresponsive polyester of claim 3, where $R^4$ is polyoxyethylene.

6. The thermoresponsive polyester of claim 3, where $R^4$ is an organic group with a functional side chain.

7. The thermoresponsive polyester of claim 1, where the thermoresponsive polyester includes a unit defined by the formula where each $R^1$ is individually a hydrocarbon group, $R^2$ is a hydrocarbon group, each $R^4$ is individually an organic group, M is a pendant functional group, and both $R^3$ groups are part the second amide group, and is selected from the group consisting of

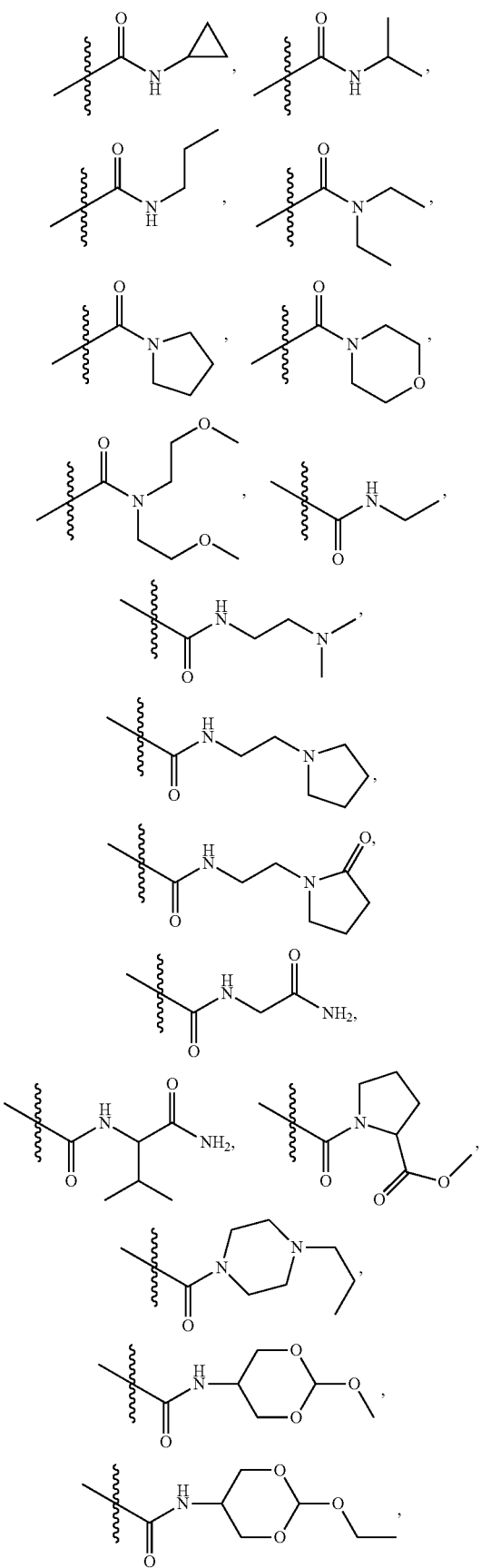

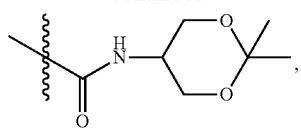

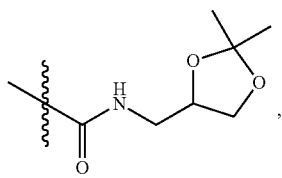

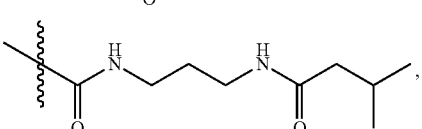

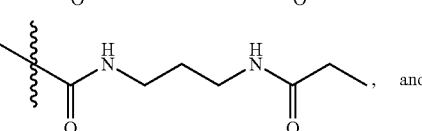

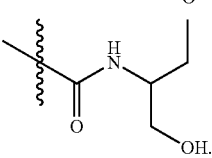

8. The thermoresponsive polyester of claim 1, where the thermoresponsive polyester is in a coacervate.

9. A composition comprising:

an aqueous solution, and dispersed in the aqueous solution a thermoresponsive polyester in a coacervate, the thermoresponsive polyester comprising a first amide group having a nitrogen atom and a carbonyl group; a second amide group tethered directly or indirectly through an organic group at the carbonyl group of the first amide group; and the nitrogen atom of the first amide group is part of the backbone of the polyester.

10. The composition of claim 1, where the thermoresponsive polyester includes a unit defined by the formula

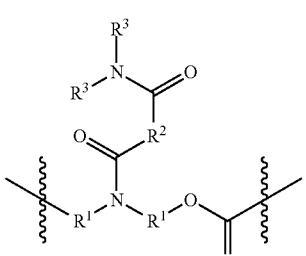

where each $R^1$ is individually a hydrocarbon group, $R^2$ is a hydrocarbon group, and each $R^3$ is individually a hydrogen atom or an organic group, or where both $R^3$ groups join to form an organic group.

11. The composition of claim 9, where the thermoresponsive polyester includes a unit defined by the formula

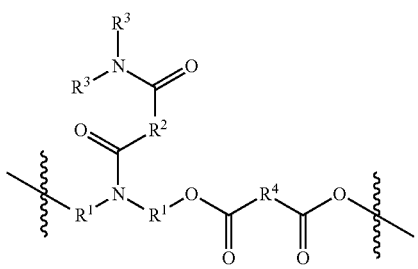

where each R¹ is individually a hydrocarbon group, R² is a hydrocarbon group, R⁴ is an organic group, and each R³ is a hydrogen atom or an organic group, or where both R³ groups join to form an organic group.

12. The composition polyester of claim 9, where the thermoresponsive polyester includes a unit defined by the formula

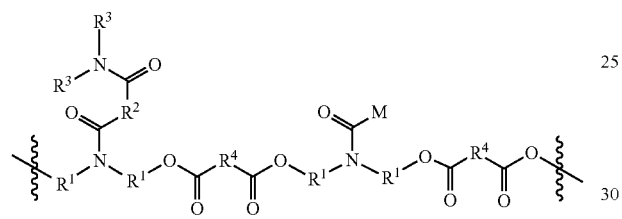

where each R¹ is individually a hydrocarbon group, R² is a hydrocarbon group, each R⁴ is individually an organic group, M is a pendant functional group, and each R³ is individually a hydrogen atom or an organic group, or where both R³ groups join to form an organic group.

13. The composition of claim 9, where the coacervate encapsulates a small molecule, an oligomer, or a macromolecule.

14. A thermoresponsive polyester comprising:
units derived from a dicarboxylic acid; and
units derived from an amide functional diol compound comprising a first amide group having a nitrogen atom and a carbonyl group; a second amide group tethered directly or indirectly through an organic group at the carbonyl group of the first amide group; and two organic groups terminated with a hydroxyl group attached to the nitrogen atom of the first amide group; where the second amide group is selected from the group consisting of

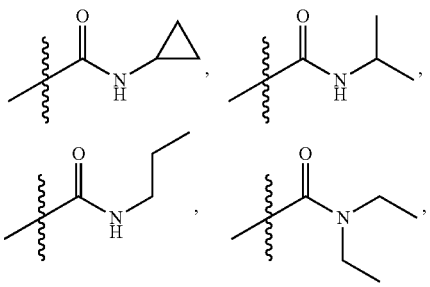

-continued

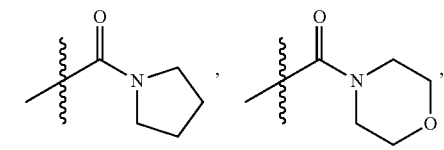

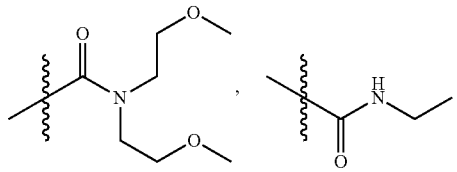

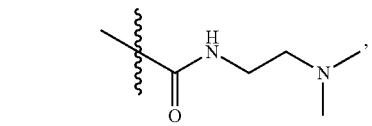

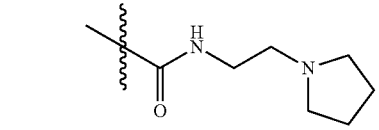

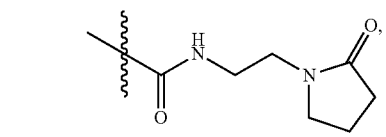

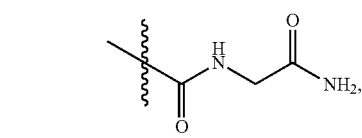

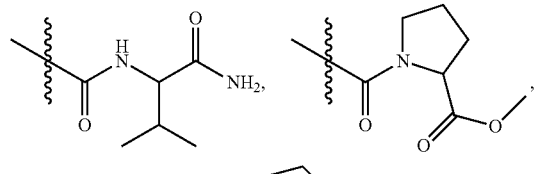

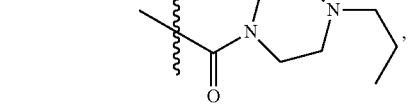

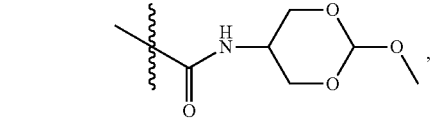

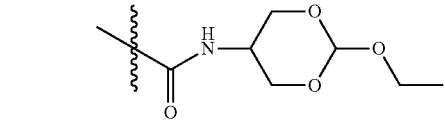

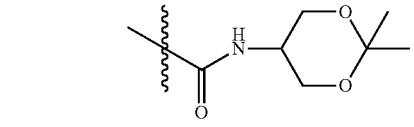

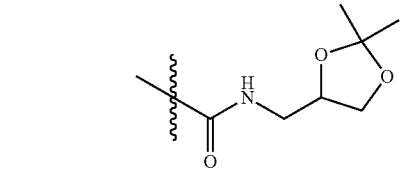

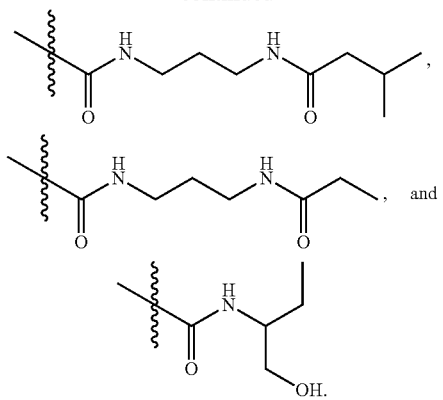

, and

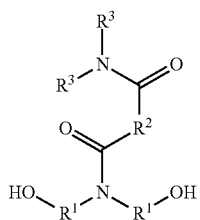

15. The thermoresponsive polyester of claim 14, where the amide functional diol compound is defined by the formula:

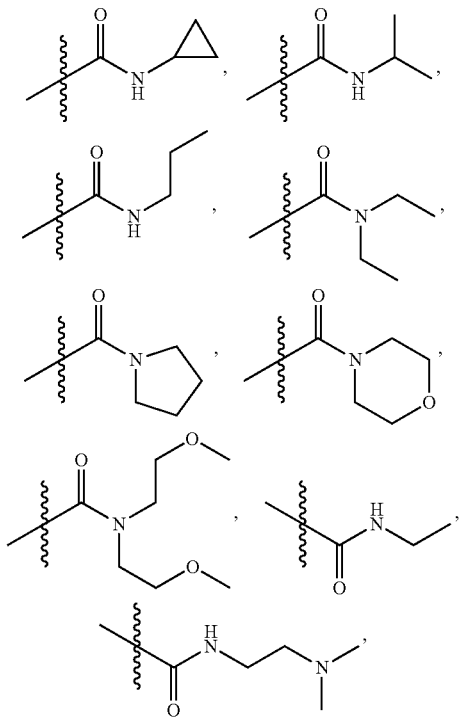

where each $R^1$ is individually a hydrocarbon group, $R^2$ is a hydrocarbon group, and both $R^3$ groups are part the second amide group, and is selected from the group consisting of

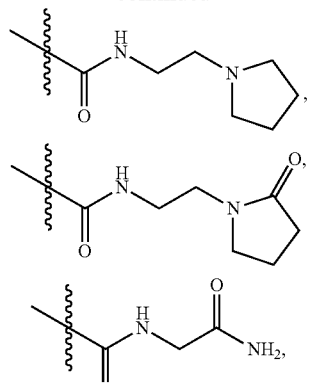

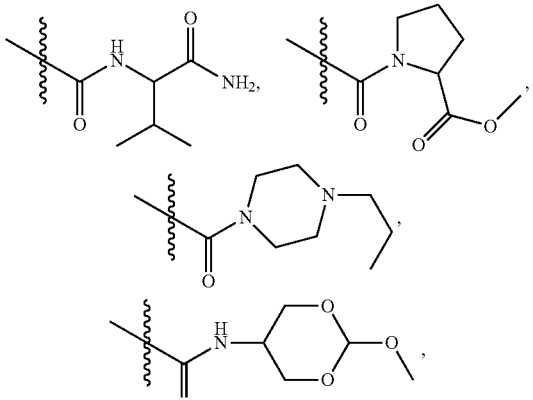

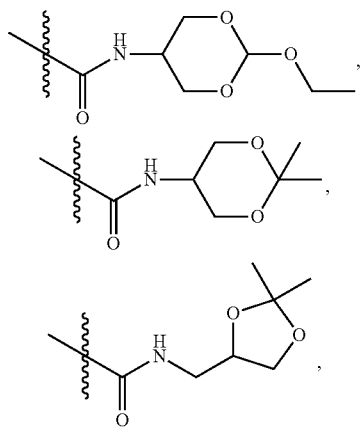

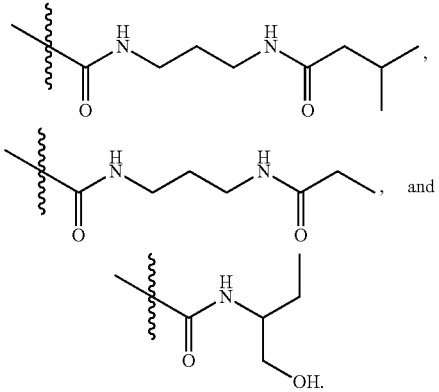

, and

16. The thermoresponsive polyester of claim 14, where the dicarboxylic acid is defined by the formula:

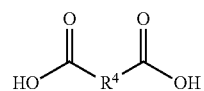
where $R^4$ is an organic group.
17. The thermoresponsive polyester of claim 14, where the thermoresponsive polyester further includes a functional diol compound derived from the formula
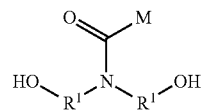
where each $R^1$ is individually a hydrocarbon group and M is a pendant functional group.
* * * * *